United States Patent [19]

Hadlaczky

[11] Patent Number: 5,891,691
[45] Date of Patent: Apr. 6, 1999

[54] METHOD OF PRODUCING A CELL CARRYING AN EXCESS OF MAMMALIAN CENTROMERES AND THE CELL LINE CARRYING AN EXCESS OF MAMMALIAN CENTROMERES

[75] Inventor: Gyula Hadlaczky, Szeged, Hungary

[73] Assignee: The Biological Research Center of the Hungarian Academy of Sciences, Hungary

[21] Appl. No.: 734,344

[22] Filed: Oct. 21, 1996

Related U.S. Application Data

[63] Continuation of Ser. No. 375,271, Jan. 19, 1995, Pat. No. 5,712,134, which is a continuation of Ser. No. 80,097, Jun. 23, 1993, abandoned, which is a continuation of Ser. No. 892,487, Jun. 3, 1992, abandoned, which is a continuation of Ser. No. 521,073, May 9, 1990, abandoned.

[51] Int. Cl.$^6$ ..................................................... C12N 5/10
[52] U.S. Cl. ..................... 435/172.3; 435/325; 435/352; 435/354
[58] Field of Search .............................. 435/325, 172.3, 435/354, 352

[56] References Cited

U.S. PATENT DOCUMENTS

| | | | |
|---|---|---|---|
| 4,518,584 | 5/1985 | Mark et al. | 424/85.2 |
| 4,608,339 | 8/1986 | Yoakum et al. | 435/6 |
| 4,684,611 | 8/1987 | Schilperoort et al. | 435/172.3 |
| 4,686,186 | 8/1987 | Sugden | 435/243 |
| 4,784,737 | 11/1988 | Ray et al. | 435/172.1 |
| 4,806,476 | 2/1989 | Coons et al. | 435/172.2 |
| 4,873,191 | 10/1989 | Wagner et al. | 435/172.3 |
| 4,935,350 | 6/1990 | Patel et al. | 435/69.4 |
| 4,970,162 | 11/1990 | Aksamit | 435/346 |
| 4,997,764 | 3/1991 | Dalla Favera | 435/70.21 |
| 5,019,034 | 5/1991 | Weaver et al. | 604/20 |
| 5,021,344 | 6/1991 | Armau et al. | 435/172.3 |
| 5,118,620 | 6/1992 | Armau et al. | 435/172.3 |
| 5,144,019 | 9/1992 | Rossi et al. | 536/23.1 |
| 5,149,796 | 9/1992 | Rossi et al. | 536/23.2 |
| 5,162,215 | 11/1992 | Bosselman et al. | 435/172.3 |
| 5,215,914 | 6/1993 | Lo et al. | 435/252.1 |
| 5,223,263 | 6/1993 | Hostetler et al. | 424/450 |
| 5,240,840 | 8/1993 | Feinberg et al. | 435/172.3 |
| 5,240,846 | 8/1993 | Collins et al. | 435/371 |
| 5,260,191 | 11/1993 | Yang | 435/6 |
| 5,266,600 | 11/1993 | Tenmyo et al. | 514/691 |
| 5,272,262 | 12/1993 | Rossi et al. | 536/23.2 |
| 5,288,625 | 2/1994 | Hadlaczky | 435/172.2 |
| 5,292,658 | 3/1994 | Cormier et al. | 435/252.33 |
| 5,298,429 | 3/1994 | Evans et al. | 436/501 |
| 5,324,655 | 6/1994 | Kriegler et al. | 435/357 |
| 5,354,674 | 10/1994 | Hodgson | 435/172.3 |
| 5,358,866 | 10/1994 | Mullen et al. | 435/357 |
| 5,364,761 | 11/1994 | Ariga | 435/6 |
| 5,396,767 | 3/1995 | Suzuki | 60/298 |
| 5,409,810 | 4/1995 | Larder et al. | 435/5 |
| 5,413,914 | 5/1995 | Franzusoff | 435/23 |
| 5,418,155 | 5/1995 | Cormier et al. | 435/189 |
| 5,424,409 | 6/1995 | Ely et al. | 536/23.71 |
| 5,434,086 | 7/1995 | Collins et al. | 436/125 |
| 5,436,392 | 7/1995 | Thomas et al. | 800/205 |
| 5,449,604 | 9/1995 | Schellenberg et al. | 435/6 |
| 5,453,357 | 9/1995 | Hogan | 435/7.21 |
| 5,457,182 | 10/1995 | Weiderrecht et al. | 530/402 |
| 5,461,032 | 10/1995 | Krapcho et al. | 514/12 |
| 5,468,615 | 11/1995 | Chio et al. | 435/7.2 |
| 5,468,634 | 11/1995 | Liu | 435/348 |
| 5,470,708 | 11/1995 | Yang et al. | 435/6 |
| 5,470,730 | 11/1995 | Greenberg et al. | 435/172.3 |
| 5,482,928 | 1/1996 | De Bolle et al. | 514/12 |
| 5,489,520 | 2/1996 | Adams et al. | 435/172.3 |
| 5,491,075 | 2/1996 | Desnick et al. | 435/69.7 |
| 5,496,731 | 3/1996 | Xu et al. | 435/320.1 |
| 5,501,662 | 3/1996 | Hofmann | 604/20 |
| 5,501,967 | 3/1996 | Offringa et al. | 435/172.3 |
| 5,503,999 | 4/1996 | Jilka et al. | 435/172.3 |

FOREIGN PATENT DOCUMENTS

| | | |
|---|---|---|
| 0240373 | 10/1987 | European Pat. Off. . |
| 1240373 | 10/1987 | European Pat. Off. . |
| 0254315 A2 | 1/1988 | European Pat. Off. . |
| 0254315 A3 | 1/1988 | European Pat. Off. . |
| 0254315 B1 | 1/1988 | European Pat. Off. . |
| 0350052 | 1/1990 | European Pat. Off. . |
| 0375406 | 6/1990 | European Pat. Off. . |
| 0375406 A2 | 6/1990 | European Pat. Off. . |
| 0473253 | 3/1992 | European Pat. Off. . |
| WO/9100358 | 1/1991 | WIPO . |
| WO/9419456 | 9/1994 | WIPO . |
| WO/9500178 | 1/1995 | WIPO . |
| WO/9507643 | 3/1995 | WIPO . |
| WO/9514769 | 6/1995 | WIPO . |
| WO/9520044 | 7/1995 | WIPO . |
| 9532297 | 11/1995 | WIPO . |

OTHER PUBLICATIONS

Brown et al., Mammalian artificial chromosomes, *Current Opinion: Genetics and Devt. 6*: 281–288 (1996).

Chisari et al., A transgenic mouse model of the chronic hepatitis B surface antigen carrier state, *Science 230*: 1157–1160 (1985).

Henikoff et al., Position–effect variegation after 60 years, *Trends in Genetics 6: 422–426* (1990).

Kappel et al., Regulating gene expression in transgenic animals, *Current Biology*, pp. 548–553, (1992).

(List continued on next page.)

*Primary Examiner*—Johnny F. Railey, II
*Attorney, Agent, or Firm*—Stephanie L. Seidman; Heller Ehrman White & McAuliffe

[57] ABSTRACT

DNA fragments and methods for obtaining them are disclosed which when put into mammalian cells together with a dominant marker gene are able to form functional centromeres. The sequences can be used to generate probes for these centromeres. Cell lines containing the functional centromeres are also provided. Methods are taught for isolating mammalian centromeric DNA as well as for producing cell lines carrying an excess of mammalian centromeres linked to a dominant selectable marker gene.

11 Claims, 18 Drawing Sheets

OTHER PUBLICATIONS

Kereso et al., Regulating gene expression in transgenic animals, *Current Biology*, pp. 548–553, (1992).

Klotman et al. Transgenic models of HIV–1, *Current Sci Ltd.* 9:313–324, (1995).

Larsson et al. Reduced β2–microglobulin mRNA levels in transgenic mice expressing a designed hammerhead ribozyme, *Nucleic Acids Research* 22:2242–2248, (1994).

Strojek et al. The use of transgenic animal techniques for livestock improvement,*Genetic Engineering: Principles and Methods 10*: 221–246, (1988).

Dialog Abstract 007268905, citing: EP 0240 373 A1.

Dialog Abstract 007389041, citing: EP 0254 315.

Baker et al., "Suppression of human colorectal carcinoma cell growth by wild–type p53", *Science* 249:912–915, (1990).

Biggin et al., "Buffer gradient gels and $^{35}$S label as an aid to rapid DNA sequence determination", *Proc. Natl. Acad. Sci. USA*, 80:3963–3965, (1983).

Blackburn, et al., "The Molecular Structure of Centromeres and Telomeres", *Ann. Rev. Biochem*, 53:163–194, (1984).

Blattner et al., "Charon phages: Safer derivatives of bacteriophage lambda for DNA cloning", *Science* 196:16, (1977).

Bostock and Christie, "Analysis of the frequency of sister chromatid exchange in different regions of chromosomes of the Kangaroo rat (*Dipodomys ordii*)", *Chromosoma*. 56:275–287, (1976).

Bostock and Clark, "Satellite DNA in large marker chromosomes of methotrexate–resistant mouse cells", *Cell* 19:709–715, (1980).

Bower, et al., "Constructing a Fully Defined Human Minichromosome" (Conference abstract), source: *Eur. Cong. Biotechnol.* 3:571, (1987).

Brazolot, et al., "Efficient transfection of chicken cells by lipofection and introduction of transfected blastoderm cells into the embryo", *Mol. Repro. Dev.* 30:304–312, (1993).

Brewer and Fangman, "The localization of replication origins on ARS plasmsids in *S. cerevisiae*", *Cell* 51:463–471, (1987).

Brisson and Hohn, "[27] Plant virus vectors: Cauliflower mosaic vectors", *Methods for Plant Molecular Biology*, Weissbach et al., eds., Academic Press, N.Y. Section VIII, pp. 437–446, (1988).

Brown, "Mammalian artificial chromosomes", *Curr. Opin. Genes Dev.* 2:479–486, (1992).

Bullock and Botchan, "Molecular events in the excision of SV40 DNA from the chromosomes of cultured mammalian cells", In: *Gene Amplification.*, Schimke RT, ed. Cold Spring Harbor, NY: Cold Spring Harbor Laboratory Press, pp. 215–224, (1982).

Burhans et al., "Identification of an origin of bidirectional DNA replication in mammalian chromosomes", *Cell* 62:955–965, (1990).

Burhans and Huberman, "DNA replication origins in animal cells—a question of context?" *Science* 263: 639–640, (1994).

Burke, et al., "Cloning of Large Segments of Exogenous DNA Into Yeast by Means of Artificial Chromosome Vectors," *Science*, 236:806–812.

Carine, et al., "Chinese Hamster Cells with Minichromosome Containing the Centromere Region of Human Chromosome 1", *Som. Cell & Mol. Gen.*, 12(5):479–491, (1986).

Carine, et al., "Molecular Characerization of Human Minichromosomes With Centromere From Chromosome 1 in Human–Hamster Hybrid Cells", *Somatic Cell and Molecular Genetics*, 15(5):445–460, (1989).

Carrano and Wolff, "Distribution of sister chromatid exchanges in the euchromatin and heterochromatin of the Indian muntjac", *Chromosoma* 53:361–369, (1975).

Chalfie, et al., Green fluorescent protein as a marker for gene expression, *Science* 263:802–804, (1994).

Chang, et al., "Ribozyme–mediated site–specific cleavage of the HIV–1 genome", *Clin. Biotech.* 2:23–31, (1990).

Chen, et al., "High–efficiency transformation of mammalian cells by plasmid DNA", *Mol. Cell. Biol.* 7:2745–2752, (1987).

Chen, et al., "Genetic mechanism of tumor suppression by the human p53 gene", *Science* 250:1576, (1990).

Chikashige, et al., "Composite motifs and repeat symmetry in S. pombe centromeres: Direct analysis by integration of Notl restriction sites", *Cell* 57:739–751, (1989).

Church, "Replication of chromatin in mouse mammary epithelial cells grown in vitro", *Genetics* 52:843–849, (1965).

Clarke, et al., "The Structure and Function of Yeast Centromeres", *Ann Rev. Genet.* 19:29–56, (1985).

Colbère–Garapin et al., "A new dominant hybrid selective marker for higher eukaryotic cells", *J. Mol. Biol.* 150:1–14; (1981).

Collins and Newlon, "Chromosomal DNA replication initiates at the same origins in meiosis and mitosis", *Mol Cell Biol* 14:3524–3534, (1994).

Cooper and Tyler–Smith, "The putative centromere–forming sequence of λCM8 is a single copy sequence and is not a component of most human centromeres", *Hum. Mol. Gen.* 1(9):753–754, (1992).

Couto, et al., "Inhibition of intracellular histoplasma capsulatum replication by murine macrophages that produce human defensin", *Infect. Immun.* 62:2375–2378, (1994).

Cram, et al., "Polyamine buffer for bivariate human flow cytogenetic analysis and sorting", *Methods in Cell Biology* 33:377–382, (1990).

Current state of the art, *Chromos Molecular Systems—News Release* (May 29, 1996) (available at http://www.chromos.com/contents.html).

Cutler, "Electroporation: Being developed to transform crops", *Ag Biotechnology News*7:3, (Sep./Oct. 1990).

Davidson, et al., "Improved techniques for the induction of mammalian cell hybridisation by polyethylene glycol", *Somatic Cell. Genet.* 2:165–176, (1976).

Dean, et al. "Multiple mutations in highly conserved residues are found in mildly affected cystic fibrosis patients", *Cell* 61:863–870, (1990).

DePamphilis, "Eukaryotic DNA replication: Anatomy of an origin", *Annu. Rev. Biochem.* 62:29–63, (1993).

Dieken, et al., "Efficient modification of human chromosomal alleles using recombination–proficient chicken/human microsell hybrids", *Nature Genet.* 12:174–182, (1996).

Dunckley, et al., "Retroviral–mediated transfer of a dystrophin minigene into mdx mouse myoblasts in vitro", *FEBS Lett.* 296:128–34, (1992).

Erlich, et al., "Recent advances in the polymerase chain reaction", *Science* 252:1643–1651, (1991).

Etches, et al., "Chimeric chickens and their use in manipulation of the chicken genome", *Poultry Sci.* 72:882–889, (1993).

Fangman and Brewer, "A question of time: replication origins of eukaryotic chromosomes", *Cell* 71:363–366, (1992).

Farr, et al., "Generation of a human X–derived minichromosome using telomere–associated chromosome fragmentation", *EMBO J*. 14:5444–5454, (1995).

Farrel, et al., "p53 is frequently mutated in Burkitt's lymphoma cell lines", *EMBO J*. 10:2879–2887, (1991).

Fátyol, et al., "Cloning and molecular characterization of a novel chromosome specific centromere sequence of Chinese hamster", *Nucl. Acids Res*. 22:3728–3736, (1994).

Fechheimer, et al., "Transfection of mammalian cells with plasmid DNA by scrape loading and sonication loading", *Proc. Natl. Acad. Sci. USA* 84:8463–8467, (1987).

Ford and Fried, "Large inverted duplications are associated with gene amplification", *Cell* 45:425–430, (1986).

Fournier, "A general high–efficiency procedure for production of microcell hybrids", *Proc. Natl. Acad. Sci.USA* 78:6349–6353, (1981).

Frasier, et al., "Efficient incorporation of transfected blastodermal cells into chimeric chicken embroyos", *Int. J. Dev. Biol*. 37:381–385, (1993).

French, et al., "Construction of a retroviral vector incorporating mouse VL30 retrotransposon–derived, transcriptional regulatory sequences", *Anal. Biochem*. 228:354–355, (1995).

Frohman and Martin, "Cut, paste, and save: new Approaches to altering specific genes in mice", *Cell* 56:145–147, (1989).

Fromm, et al., "Expression of genes transferred into monocot and dicot plant cells by electroporation", *Proc. Natl. Acad. Sci.USA* 82:5824–5828, (1985).

Gillespie, et al., "Tissue–specific expression of human CD4 in transgenic mice", *Mol. Cell. Biol*. 13:2952–2958, (1993).

Gluzman, "SV40–transformed simian cells support the replication of early SV40 mutants", *Cell* 23:175–182, (1981).

Goodfellow, et al., "Techniques for mammalian genome transfer", in *Genome Analysis a Practical Approach*, K.E. Davies, ed., IRL Press, Oxford, Washington DC. pp. 1–17 (1989).

Graham and van der Eb, "A new technique for the assay of infectivity of human adenovirus 5 DNA", *Virology* 52:456–457, (1973).

Green, et al., "Chromosomal region of the cystic fibrosis gene in yeast artificial chromosomes: A model for human genome mapping", *Science* 250:94–98.

Grierson, et al. *Plant Molecular Biology*, 2d Ed., Blackie, London, Ch. 7–9, (1988).

Gritz, et al., "Plasmid–encoded bygromycin B resistance: the sequence of hygromycin B phosphotransferase gene and its expression in *Escherichia coli* and *Saccharomyces cerevisiae*", *Gene* 25:179–188, (1983).

Guide to Techniques in Mouse Development, *Methods in Enzymology* 25:803–932, (1993).

Gunning, et al., "A human β–actin expression vector system directs high–level accumulation of antisense transcripts", *Proc. Natl. Acad. Sci.USA* 84:4831–4835, (1987).

Haase, et al., "Transcription inhibits the replication of autonomously replicating plasmids in human cells", *Mol. Cell. Biol*. 14:2516–2524, (1994).

Hadlaczky, et al., "Centromere formation in mouse cells cotransformed with human DNA and a dominant marker gene", *Proc. Natl. Acad. Sci.USA* 88:8106–8110, (1991).

Hadlaczky, et al., "Centromere proteins: I. Mitosis specific centromere antigen recognized by anti–centromere antibodies", *Chromosoma*, 97(4):282–288, (1989).

Hadlaczky, et al., "Protein depleted chromosomes", *Chromosoma* 81:537–555, (1981).

Hadlaczky, et al., "Direct evidence for the non–random localization of mammalian chromosomes in the interphase nucleus", *Exp. Cell Res*. 167:1–15, (1986).

Hadlaczky and Szalay, "Mammalian artificial chromosomes: Potential vectors for gene therapy", Abstract from International Symposium on *Gene Therapy of Cancer, AIDS and Genetic Disorders*, Trieste (Italy) (Apr. 10–13, 1996).

Hadlaczky and Szalay, "Mammalian artificial chromosomes: Introduction of novel genes into mammalian artificial chromosomes", Abstract from International Symposium on *Gene Therapy of Cancer, AIDS and Genetic Disorders*, Trieste (Italy) (Apr. 10–13, 1996).

Hadlaczky, et al., "Structure of isolated protein–depleted chromosomes of plants". *Chromosoma* 86:643–659, (1982).

Hadlaczky, "Structure of metaphase chromosomes of plants", *Internatl. Rev. Cytol*. 94:57–76, (1985).

Hall, et al., "Expression and regulation of *Escherichia coli lacZ* gene fusions in mammalian cells", *J. Mol. Appl. Gen*. 2:101–109, (1983).

Handeli, et al., "Mapping replication units in animal cells", *Cell* 57:909–920, (1989).

Hanna, et al., "Specific expression of the human CD4 gene in mature CD4+ CD8– and immature CD4+ CD8+ T cells and in macrophages of transgenic mice", *Mol. Cell. Biol*. 14:1084–1094, (1994).

Harper, et al., "Localization of single copy DNA Sequences on G–banded human chromosomes by in situ hybridization", *Chromosoma* 83:431–439, (1981).

Hassan, et al., "Replication and transcription sites are colocalized in human cells", *J. Cell. Sci*. 107:425–434, (1994).

Hilwig and Gropp, "Decondensation of constitutive heterochromatin in L cell chromosomes by a benzimidazole compound (33258 Hoechst)", *Exp Cell Res* 81:474–477, (1973).

Hogan, et al., *Manipulating the Mouse Embryo: A Laboratory Manual*, Cold Spring Harbor Laboratory Press, Cold Spring Harbor, NY, pp. 253–289, see, especially pp. 255–264 and Appendix 3, (1994).

Hollo, et al., "Evidence for a megareplicon covering megabases of centrome segments", *Chromosome Research* 4:1–14, (1996).

Holmquist and Comings, "Sister chromatid exchange and chromosome organisation based on a bromodeoxyuridine Giemsa–C–banding technique (TC–banding)", *Chromosoma*52:245–259, (1975).

Hsu and Markvong, "Chromosomes and DNA in Mus: Terminal DNA systhetic sequences in three species", *Chromosoma* 51:311–322, (1975).

Huberman and Riggs, "On the mechanism of DNA replication in mammalian chromosomes", *J Mol Biol* 32:327–341, (1968).

Huberman, et al., "The in vivo replication origin of the yeast 2 µm plasmid", *Cell* 51:473–481, (1987).

Huxley, "Mammalian artificial chromosomes: a new tool for gene therapy", *Gene Therapy*, 1:7–12, (1994).

Hyde, et al., "Correction of the ion transport defect in cystic fibrosis transgenic mice by gene therapy", *Nature* 362:250–255, (1993).

Hyrien, et al., "The multicopy appearance of large inverted duplication and the sequence at the inversion joint suggest a new model for gene amplification", *EMBO J* 7:407–417, (1988).

Ish–Horowitz, et al., "Rapid and efficient cosmid cloning", *Nucleic Acids Res*. 9:2989–2998, (1981).

Jabs, et al., "Characterization of a cloned DNA Sequence that is present at centromeres of all human autosomes and the X chromosome and shows polymorphic variation", *Proc. Natl. Acad.* 81:4884–4888, (1984).

Jacob, et al., "On the regulation of DNA replication in bacteria", *Cold Spring Harb Symp Quant Biol* 28:329–348, (1963).

Joy and Gopinathan, "Expression of microinjected foreign DNA in the silkworm", *Bombex mori, Current Science* 66:145–150, (1991).

Keown, et al., "Methods for introducing DNA into mammalian cells", *Meth. Enzymol.* 185:527–537, (1990).

Kerem, et al., "Identification of the cystic fibrosis gene: genetic analysis", *Science* 245:1073–1080, (1989).

Kereso, et al., "De novo chromosome formations by large-scale amplification of the centromeric region of mouse chromosomes", *Chromosome Research* 4:1–14, (1996).

Kitsberg, et al., "Replication structure of the human b–globin gene domain", *Nature* 366:588–590, (1993).

Korenberg, et al., "Human genome organization: Alu, Lines, and the molecular structure of metaphase chromosome bands", *Cell* 53:391–400, (1988).

Kornberg and Baker, *"DNA Replication"*, 2nd. ed., New York: W.H. Freeman and Co, p. 474, (1992).

Lambert, et al., "Functional complementation of ataxia–telangiectasia group D (AT–D) cells by microcell–mediated chromosome transfer and mapping of the AT–D locus to the region 11q22–23", *Proc. Natl. Acad. Sci. USA* 88:5907–59, (1991).

Lawrence, et al. "Sensitve, high–resolution chromatin and chromosome mapping in situ: Presence and orientation of two closely integrated copies of EBV in a lymphoma line", *Cell* 52:51–61, (1988).

Le Bolc'h, et al., "Cationic phosphonolipids as non viral vectors for DNA transfection", *Tetrahedron Lett.* 36:6681–6684, (1995).

Leder, et al., "EK2 derivatives of bacteriophage lambda useful in the cloning of DNA from higher organisms: the λgtWES system", *Science* 196:175–177, (1977).

Liu, et al., "The pro region of human neutrophil defensin contains a motif that is essential for normal subcellular sorting", *Blood* 85:1095–1103, (1995).

Locardi, et al., "Persistent infection of normal mice with human immunodeficiency virus", *J. Virol.* 66:1649–1654, (1992).

Looney, et al., "The dihydrofolate reductase amplicons in different methotrexate–resistant Chinese hamster cell lines share at least a 273–kilobase core sequence, but the amplicons in some cell lines are much larger and remarkably uniform in structure", *Mol. Cell Biol.* 8:5268–5279, (1988).

Lorenz, et al., "Isolation and expression of a cDNA encoding *Renilla reniformis* luciferase", *Proc. Natl. Acad. Sci. USA* 88:4438–4442, (1991).

Lorenz, et al., "Expression of the *Renilla reniformis* luciferase gene in mammalian cells", *J. Biolum. Chemilum.* 11:31–37, (1996).

Love, et al., "Transgenic birds by microinjection", *Bio/Technology* 12:60–63, (1994).

Ma, et al., "Sister chromatid fusion initiates amplification of the dihydrofolate reductase gene in Chinese hamster cells", *Genes Develop.* 7:605–620, (1993).

Ma, et al., "Organisation and genesis of dihydrofolate reductase amplicons in the genome of a methotrexate–resistant Chinese hamster ovary cell line", *Mol. Cell Biol.* 8:2316–2327, (1988).

Madan, et al., "Fluorescence analysis of late DNA replication in mouse metaphase chromosomes using BUdR and 33258 Hoechst", *Exp. Cell Res.* 99:438–44, 91976).

Maniatis, et al., "The isolation of structural genes from libraries of eucaryotic DNA", *Cell* 15:687–701, (1978).

Mansour, et al., "Disruption of the proto–oncogene int–2 in mouse embryo–derived stem cells: a general strategy for targeting mutations to non–selectable genes", *Nature* 336:348–352, (1988).

Matthews, et al., "Purification and properties of *Renilla reiformis* ludiferase", *Biochemistry* 16:85–91, (1977).

Maxwell, et al., "Regulated expression of a diphtheria toxin A–chain gene transfected into human cells: possible strategy for inducing cancer cell suicide", *Cancer Res.* 46:4660–4664, (1986).

McGill, et al., "λCM8, a human sequence with putative centromeric function, does not map to the centromere but is present in one or two copies at 9qter", *Hum. Mol. Gen.* 1(9):749–751.

McLean, "Improved Techniques for immortalizing animal cells", *Tibtech* 11:232–238, (1993).

Meinkoth and Wahl, "Hybridization of nucleic acids immobilized on solid supports", *Anal. Biochem.* 138:267–284, (1984).

Meyne, et al., "Distribution of non–telomeric sites of the $(TTAGGG)_n$ telomeric sequence in vertebrate chromosomes", *Chromosoma* 99:3–10, (1990).

Miller, in *Experiments in Molecular Genetics*, Cold Spring Harbor Press, pp. 352–355 (1972).

Miller, "Is the centromeric heterochromatin of *Mus musculus* late replicating?" *Chromosoma* 55:165–170, (1976).

Miller and Rosman, "Improved retroviral vectors for gene transfer and expression ", *Biotechniques* 7:980–990, (1989).

Mitani, et al., "Delivering therapeutic genes—matching approach and application", *Trends Biotech.* 11:162–166, (1993).

Morgan and French Anderson, "Human gene therapy", *Annu. Rev. Biochem.* 62:191–217, (1993).

Morgenstern, et al., "Advanced mammalian gene transfer: High titre retroviral vectors with multiple drug selection markers and a complementary helper–free packaging cell line", *Nucleic Acids Res.* 18:3587–3596, (1990).

Mulligan, "The basic science of gene therapy", *Science* 260:926–932, (1993).

Murray, et al., "Construction of Artificial Chromosomes in Yeast", *Nature* 305:189–193, Sep. 1983.

Nabel, et al., "Site–specific gene expression in vivo by direct gene transfer into the arterial wall", *Science* 249:1285–1288, (1990).

Nikolaev, et al., "Microinjection of recombinant DNA into early embryos of the mulberry silkworm *Bombyx mori*", *Mol. Biol. (Moscow)* 23:1177–87, (1989).

O'Keefe, et al., "Dynamic organization of DNA replication in mammalian cell nuclei: Spatially and temporally defined replication of chromosome–specific a satellite DNA sequences", *J. Cell Biol.* 116:1095–1110, (1992).

Osborne, et al., "A mutation in the second nucleotide binding fold of the cystic fibrosis gene", *Am. J. Hum. Genetics* 48:608–612, (1991).

Paszowski and Saul, "[28]Direct gene transfer to plants", *Methods for Plant Molecular Biology*, Weissbach et al., eds., Academic Press, N.Y., Section VIII, pp. 447–463, (1988).

Perry and Wolff, "A new Giemsa method for the differential staining of sister chromatids", *Nature* 251:156–158, (1974).

Petitte, et al., "Production of somatic and germline chimeras in the chicken by transfer of early blastodermal cells", *Development* 108:185–189, (1990).

Pinkel, et al., "Cytogenetic analysis using quantitative, high-sensitivity, fluorescence hybridization", *Proc. Natl. Acad. Sci. USA*, 83:2934–2938, (1986).

Prasher, et al., "Primary structure of the *Aequorea victoria* green–fluorescent protein", *Gene* 111:229–233, (1992).

Praznovszky, et al., "De novo chromosome formation in rodent cells", *Proc. Natl. Acad. Sci. USA* 88:11042–11046, (1991).

Priest, "Cytogenetics", In *Medical Technology Series*. R.M. French, M. Eichman, B. Fiorella, and H.F. Weisberg, eds. (Lea and Febiger, Philadelphia) pp. 189–190, (1969).

Quastler, et al., "Cell population kinetics in the intestinal epithelium of the mouse", *Exp. Cell Res.* 17:420–438, (1959).

Roth, "Artifizielle chromosomen", *Natur Wissenschaften* 74:78–85, (1987).

Report and recommendations of the panel to assess the NIH investment in research on gene therapy, Orkin and Motulsky, co–chairs (Dec. 7, 1995).

Richia and Lo, "Introduction of human DNA into mouse eggs by injection of dissected chromosome fragments", *Science* 245:175–177, (1989).

Riordan, et al., "Identification of the cystic fibrosis gene: cloning and characterization of complementary DNA", *Science* 245:1066–1072, (1989).

Sumner, A simple technique for demonstrating centromeric heterochromatin, *Cell Res.* 75:304–306 (1972).

Szybalsky et al. Genetic studies with human cell lines, *Natl. Cancer Inst. Monogr.* 7:75–89 (1982).

Tamura et al., Microinjection of DNA into early embmryo of *Bombyx mori*, *Bio Ind.* 8:26–31 (1991) (Chemical Abstracts # 114(21)200502z).

Toledo et al., Co–amplified markers alternate in megabase long chromosomal inverted repeats and cluster independently in interphase nuclei at early steps of mammalian gene amplification, *EMBO J.* 11:2665–2673 (1992).

Tonghua et al., Effects of antisense epidermal growth factor and its receptor retroviral expression vectors on cell growth of human pancreatic carcinoma cell line, *Chin. Med. J.* (Beijing, Engl. Ed.) 108:653–659 (1995).

Transfection of DNA into eukaryotic cells, *Current Protocols in Molecular Biology*, vol. 1, Wiley Inter–Science, Supplement 14, Unit 9.1.1–9.1.9 (1990).

Uchimiya et al., Transgenic plants, *J. Biotechnol.* 12: 1–20 (1989).

Vig and Richards, Formation of primary constriction and heterochromatin in mouse does not require minor satellite DNA, *Exp. Cell Res.* 201:292–298 (1992).

Wang and Fedoroff, Banding of human chromosomes treated with trypsin, *Nature* 235:52–54 (1972).

Weinberg, Tumor suppressor genes, *Science* 254:1138–1146 (1991).

White et al., A frame–shift mutation in the cystic fibrosis gene, *Nature* 344:665–667 (1990).

Why are MACs in vogue, *Chromos Molecular Systems— News Release* (May 29, 1996).

Wigler et al., DNA–mediated trnsfer of the adenine phosphoribosyltransferase locus into mammalian cells, *Proc. Natl. Acad. Sci. USA* 76:1373–1376 (1979).

Willard and Waye, Hierarchical order in chromosome specific human alpha satellite DNA, *Trends Genet.* 3:192–198 (1987).

Williams and Blattner, Construction and characterization of the hybrid bacteriophage lambda charon vectors for DNA cloning, *J. Virol.* 29:555–575 (1979).

Wong et al., Sequence organisation and cytological localization of the minor satellite of mouse, *Nucl. Acids Res.* 16:11645–11661 (1988).

Yamada et al., Multiple chromosomes carrying tumor suppressor activity for a uterine endometrial carcinoma cell line identified by microcell–mediated chromosome transfer, *Oncogene* 5:1141–1147 (1990).

Yates et al., Stable replication of plasmids derived from Epstein–Barr virus in various mammalian cells, *Nature* 313:812–815 (1985).

Yates et al., A cis–acting element from the Epstein–Barr viral genome that permits stable replication of recombinant plasmids in latently infected cells, *Proc. Natl. Acad. Sci. USA* 81:3806–3810 (1984).

Yeung et al., Human CD4–major histocompatibility complex class II (Dqw6) transgenic mice in an endogenous CD4/CD8–deficient background: reconstitution of phenotype and humano–restricted function, *J. Exp. Med.* 180:1911–1920 (1994).

Yurov, Identification and characterization of two distinct polymorphic α–satellite DNA sequences from centromeric regions of the chromosomes 13 and 21 (A2299), *Cytogenet. Cell Genet.* 51:1114 (1989).

Yurov, Collection of α–satellite DNA probes: Highly polymorphic markers for centromeric regions of all human chromosomes (A2298), *Cytogenet. Cell Genet.* 51:1114 (1989).

Traver et al., Proc. Natl. Acad. Sci. USA 86(15):5898–5902 (1989).

```
         10         20         30         40         50         60         70         80         90        100
GAATTCATGC CAAGTGCAAG TCTGGGGGTC ACCTTGACTG GAGACCCTCC TCCCGCCACG TTCTTTGAAC TTCCCTCCAT CCGGTCCAAG TCTCTCCAA
        110        120        130        140        150        160        170        180        190        200
TGCCATCCTC AGCCCTGCAG CAGCCCTCAC TCCCGATGCC TTCCCACCTC CTCACCACTC TGCCCCACC TGGCCAGCCC TGGCCAGCCC ATCACCTCCA GGGCCCAACT
        210        220        230        240        250        260        270        280        290        300
TGGAGCCCCC AGGACCTCCC CGTGCCCTGC CTGATGTCCC GCCTGTCCCC ACAGAGCCTC ACTTGGTCAC CACCCAGTCC TGGCCCTTGC TTACTGTGGC
        310        320        330        340        350        360        370        380        390        400
TGCACCCCGA GGTGTCCTAG GGTCTAGCAG GTGGCTGCCC AGACATGGAG GTAGAGGAAG GAGTGGGTGG GGATGGGCTT GTCCTGCCCA GGCCTCCCTG
        410        420        430        440        450        460        470        480        490        500
CCTGTCCTGC TGGCCACAGC CTTGGCTTGC CCAGGAGAAC CCATGGGCCA CACATCCCAC TGCCAATCCC ACACGTCCTT TCTCGGGAAC ACCGTGGGGA
        510        520        530        540        550        560        570        580        590        600
AAGCTGTGGC ACCAGCTCCT TCCTTTTGCA ATCTGATGA ATCTCACCA GCCCACTCTC GGGATTTCAA GGCCCCTGGT CACACCAGGA TCATAGGCCT CCCCCATCCC
        610        620        630        640        650        660        670        680        690        700
CTGGACACAC AGAGAGACAC CTGGATTCAG GTCAGGCCTC GCCCACTCTC GGCTATATTT CTCCCCAAGC CGTGTGTCCT CAGCTGTGTA ATCAGGACCA
        710        720        730        740        750        760        770        780        790        800
TAAGGAAGTT CCCTCATAGG GTTCTTGTGA GGACGGCACG ATTTACGTAG GGGATGCTCA CACCGTGCCT GGCAGCTGGG ACGCACTCCA CCCGCGGGCAG
        810        820        830        840        850        860        870        880        890        900
CCGCGTCCCA TGGCTTCTCA GTGAGTTTTC CAGCCACACT GCACTTCTTA GACAGGAACA CTCCATACGA TGTCCCTCTC CTGCACTGGA TGGCCCAAAA
        910        920        930        940        950        960        970        980        990       1000
ATCTGAAATA AGAGGAGGAG TGCGTGTGAA GCTCCCAGTG GAGGGTTTGG CACCTGTCCA GCATGTCCCC AAGGGCAAGT CACGGCTCTG AGATTCAGTG
       1010       1020       1030       1040       1050       1060       1070       1080       1090       1100
TCTCCTTCTG CAAGTAGGGC CAATAGTGGT TCCTCCCTCC CAGGGCTGAA GTGAGGATGA GATGGGATAA TCCACCCCCG TCCCACACC CTGCAGGTCA
       1110       1120       1130       1140       1150       1160       1170       1180       1190       1200
TCATCATTGC TAGCAGTTGT GTGGTGGAGC AGGTGCTCTT GAGGGAGCGA CACCTCCAGG TGCTCCCCTG CCCTGCTGGC CCCTCTGCAG GAGGTGACAC
```

FIG. 1A

```
         1210       1220       1230       1240       1250       1260       1270       1280       1290       1300
CCAGGCCCCT TTCCCCTGGG GCAGCCAGCT CAGCCCCTCT CTCTCCCACA GGTGCCGGTG CAGTTCCTTT GGCAGTAAGT AACAGCGGCCT GGGGAGGGTG
         1310       1320       1330       1340       1350       1360       1370       1380       1390       1400
GCCAGGGCCC CCACTGCACG CGCCTCTTTG CATGTCCTGG AAAAAGCAGG AGAGAAAAAA GGGGCTTCAG TGTCCCCTCT GGGACTTGGG CCATTCACTC
         1410       1420       1430       1440       1450       1460       1470       1480       1490       1500
CCTCTCTAA TTACACCCCT ACTGCTTCTC CACCTCTCCC CCCTCCACCT CCCTCCACCC AAAAGCAGG ACTTCACATC ATATGCCGTA TAGCCATGTG
         1510       1520       1530       1540       1550       1560       1570       1580       1590       1600
TCATTTGCT GTGCCTGTGG CCCAGCAATC TCTAGGCTCT CCCAGGAGCT CCATCAGTGC TGCTTTGGAA AACGGGACAG GACTTTTTGC AGGTCTCTTG
         1610       1620       1630       1640       1650       1660       1670       1680       1690       1700
GCCCTGGGT CTCCTCCCTG CACCCACGCC ACTTCTCTCA CCTGGGATCT GGAGAGCAGT CTCTCCTGCC AGTCAAGAGT GGGGTGACCT
         1710       1720       1730       1740       1750       1760       1770       1780       1790       1800
TCCCCACCA GGCAGAATCC ACCCCCTAGC CTAACCATGG CGGCAGCCTC CCTCTGGCAG CAGCTTGTCC CAGGGCTCTG CTCGTCCAGG
         1810       1820       1830       1840       1850       1860       1870       1880       1890       1900
TCAGCTCAGG TCCCAGGGGA GTCGGACCAG GGAGGGGCAT CTGCAGGAGG TGGGGGTCCT GAGAGTTCCC CAGGAGGGCG GGCGCACAGG
         1910       1920       1930       1940       1950       1960       1970       1980       1990       2000
TTATCAGTAA ATGTCATCGA GACTGTCCCC AGACACTCAC AGGGTGCCAG GCAGTCTCTC CTTTCACCCT TGCAAACCCT CCCCTGGGAG GTCGCCATCT
         2010       2020       2030       2040       2050       2060       2070       2080       2090       2100
GCTCTGCGAG GCAGCAGGAG AGGACTGGCC AATGTCAAAG AGCCAGCCGG GAGCAGACCC CAAATCTCAG AGATGCTTCT GGGGCCGTCA CCCTCCACCA
         2110       2120       2130       2140       2150       2160       2170       2180       2190       2200
GGGCTCTGTG GGGCCCCACA TCCCACCCAA GTTGTCCCTC CCGGACCCAG GGGGCCCCTG GCTGGGAAGC CAGTGAGCCG AGAGGGCGCC AGAAAGAAGC
         2210       2220       2230       2240       2250       2260       2270       2280       2290       2300
TGGACCCTGC AGGGACGCTG GTCTGCACAG CCGTGCTAAG TTGCTTTCTT GTGGTGTCCC CACCCCGGCC AACCCCCAAC CCTCTCTTGC TTTTCCCATC
         2310       2320       2330       2340       2350       2360       2370       2380       2390       2400
TCTCACCAGG CATCAGCAGG TCCCAGAAAG ACCCCGACCC CAAAGGCCCT GTGGCACTTG CGGCCACGAG AGCCATGACA GGGCCCCCTA CTACTCCTGT
```

```
      3610        3620        3630        3640        3650        3660        3670        3680        3690        3700
AGAGAAGACC TCCTCCTTCC TAGGCCATCC AGAGCAGCTC CCTGGGCAG CACACCCAC CTCTTTCTAC ATCCTTCCTT TTCTGCAGAG CATTTACAGG
      3710        3720        3730        3740        3750        3760        3770        3780        3790        3800
AGGCATTTTC TAGCCAAAAG ATTGGAGGAT TTCCGGGAAG CCTCCTGACC CAGGAATCCT CTTTGGGGTG GAAGACATGG GTCACTCTGA GAATTCTGGA
      3810        3820        3830        3840        3850        3860        3870        3880        3890        3900
CTTCAAACAT AGGTTGGCCC AGCCACAAGG GACCTGTGCT TTGCTGATGA GCCTGTGGTG GGCAGACAGA AGCAAAAACA GTGGTGGTGG GTGCTGTGCC
      3910        3920        3930        3940        3950        3960        3970        3980        3990        4000
TGTCTCCAAA CAGGGGTTTG GCTGGAGGC CAGATACTCT CCATATCACA TGTGCAAGTG CACACATGCA CACACACACA CACATGCATG CACACACACA
      4010        4020        4030        4040        4050        4060        4070        4080        4090        4100
GGCATGCACA CGCACACACA CACACAGAGG AATCCATTTG CAGAGCTGCT TCTGACTTGG TGCCAGGGCC AGCCGTGGGA GGCTGGGCAG
      4110        4120        4130        4140        4150        4160        4170        4180        4190        4200
ATTGTGCAAG TTGGGAATTA AAGAGGAAAA GTCAGAGGCC AGAGTGGGAA ATGCAGGGGA GTTGAGGGTC CCCAGGACCC TCAGTGAGCA GAAGGCACAC
      4210        4220        4230        4240        4250        4260        4270        4280        4290        4300
CCTCTCGGCA AGACAGTGCT GCTCTGCACC TAGCCCTGTA TCAAGAAGCA GGACATTAGG GGAGGAGGTG GCTCCAATGT GACAGCCAGT GGCCCCTACA
      4310        4320        4330        4340        4350        4360        4370        4380        4390        4400
CCACACATCTA GGGGCTCCTC CCTCCTCTTC AGCAACTGAA GCCCCTGTCC AGAGCCCCCA TTAATGAAAA CGATCATTGC AGTAGCTGAG GGTGAGTTCT
      4410        4420        4430        4440        4450        4460        4470        4480        4490        4500
GCCACACATCTA GGGGCTCCTC CCTCCTCTTC AGCAACTGAA GCCCCTGTCC AGAGCCCCCA TTAATGAAAA CGATCATTGC AGTAGCTGAG GGTGAGTTCT
      4410        4420        4430        4440        4450        4460        4470        4480        4490        4500
CCTGGGCTGT GCTCGTATGA TTGTATCATC ATATCATTGT ATTCTGGGCT CACAGCTCCG TGAGATGGAG GCTGTTATTT TCCTAGTCCC ACAGGTGAGG
      4510        4520        4530        4540        4550        4560        4570        4580        4590        4600
GGATCGAGGC TTAGGAAGAA GCAGCTGGAT TTTATGATAT GTAAAATTAC ACCTCAATCA AGCTGTTTCA GAAGAAAAAA GGGGCAGCTG CTCAAGGTCT
      4610        4620        4630        4640        4650        4660        4670        4680        4690        4700
CAGAATTATG GAGAGGCACG GGCAGGATTT GAACTCAGGG CTCGCCAACT CAGCCACCCA AAGCTATTGT CCTGAGGCCT CCAGGGCTA TGAGGTAGAG
      4710        4720        4730        4740        4750        4760        4770        4780        4790        4800
CTATCTTTTT TTTTTTTTTT TTGAGATGGA GTTTCGCTCT TGTCGCTGAG GCTGGAGTGC AATGGAGCAA TCTCAGCTCA CTGCAACCTC CGCCCCCCA
```

FIG. ID

```
4810        4820        4830        4840        4850        4860        4870        4880        4890        4900
GGTTCAAGCA  ATTCTCCTGC  CTCAGCCTCC  CGAGTAGCTG  GGATTACAGG  CACCTGTCAC  CATGTTCAGC  TACTTTTTGT  CTTTTTAGAG  AGACAGGGTT
    4910        4920        4930        4940        4950        4960        4970        4980        4990        5000
TCACCATGTT  GGTCAGGCTG  GTGTTGAACT  CCTGACCTCA  AGTGATCCAC  CCGCCTCAGC  CTCCCAAAGT  GCTGGGATTC  CAGGCGTGAG  CCACCGCACC
    5010        5020        5030        5040        5050        5060        5070        5080        5090        5100
CGGCCAAGTA  GTGCTGTCTC  CAAGGCCTGG  CTTGCAGGGC  TTCCCAGTTC  CAAAGGAGCA  GACCGGGCTT  CCATGGGGCC  TTGGCACAGC  ACACAGGCCA
    5110        5120        5130        5140        5150        5160        5170        5180        5190        5200
TGGCGAGAAC  TTGCTTCCCA  CACACCTGAG  TGTGTCCCTG  GGCAGCCAAA  GCCAGGACTC  CCTCCCTCCC  CAAGACCCTG  GTCCCTGAAA  GATCCTGAAT
    5210        5220        5230        5240        5250        5260        5270        5280        5290        5300
ACCCCCGAGT  GCCTCCCAAC  AGGTGCTTCG  GGCTCTTTGA  ACAGAGTCCA  GCTGGGCCTC  GGCCAGATGT  TTCTCCCGCC  TTCTCCCGCC  TGCCAATGTC
    5310        5320        5330        5340        5350        5360        5370        5380        5390        5400
AAGCTGTCTG  GAGGACAGCG  CTGCGGCGCG  GAAAACGCGC  TGGAGACACT  AATCCTTTCC  TGGGCTGGGC  ACGGAGGATG  GAGGGAGACA  GGCTCTGAAG
    5410        5420        5430        5440        5450        5460        5470        5480        5490        5500
CAAATGCCTT  CAGGGCTGGC  TTTCTCATGG  CTCTAATTAA  GCCTGCAATT  TGGGCCTGGC  GCTCATCTTC  CCACTGAACA  TCATAATTAA  AGTCAATTCA
    5510        5520        5530        5540        5550        5560        5570        5580        5590        5600
GTGTCCAAAG  CTCCCCGCTC  CCAGCTGGAA  GTCTTCGCAC  TTGTTAGCTG  GTAGCTTTCC  TTTCTTCCCC  ACAGCCACCG  TTGTGTATAA  TCCCTTCAAG
    5610        5620        5630        5640        5650        5660        5670        5680        5690        5700
AAGCGAAAAC  AGCAGGCGCT  CCCTGTCCTC  TGGTTGTCCT  TTGAAAATTTG  GCACAGGCAG  TTCTTTGCCA  GCCCTGCCTG  CCTGCCTTGC  TGGCTGTGTG
    5710        5720        5730        5740        5750        5760        5770        5780        5790        5800
TCCCGTTAGT  CTACGGGCTG  AGCGTTGTGT  CACTGGTTCA  TGCTGGGGTC  CCTGGTGAAA  ATGGGCCAGG  CCAGGGGTCA  GGAAGGTAGA  AGGGCAGTGA
    5810        5820        5830        5840        5850        5860        5870        5880        5890        5900
TCAGGGAAGC  AGGTCAGATG  CTGGGGAAGG  CTCCCGGTCCC  TGGATTGCGG  CTGGACAGGA  AGGACACCTT  CCAGGACACT  TCTGGACACA  TGTAAGATCT
    5910        5920        5930        5940        5950        5960        5970        5980        5990        6000
TGGCCGGAAG  AGATGTCCCA  CTTCCGCAGCC  ATGTAGCCAG  AGAGATCAGC  TCAGAGAGGT  AGGCCCAG  CTGGGCCCAG  AGGCGGGACC  TGGTCGTAGC  TCTGTCCTTC
```

FIG.IE

```
         6010       6020       6030       6040       6050       6060       6070       6080       6090       6100
AGTCAGAACG GGGACGGGCA CAGGGAGTGT AGAAGGGTCT CGCTGAAGAA GTATGCAGAT TCTCAGGCGA TGGGTTCACC TCTCATCTAT CGGGCTTTAA
         6110       6120       6130       6140       6150       6160       6170       6180       6190       6200
GTCTGCATGT GCCCTCCACA GGCTAAATAG TGTAGATGCT GCCTATGTAG TAGATTTGGA CCCAATTCCT TTGGCCATGT AGACAGAGCC TCTCCTTATA
         6210       6220       6230       6240       6250       6260       6270       6280       6290       6300
GTGCTGCTGC TTCTAAGGGG CCTGTGGGTA GCGGGGCTGT GATGCCTCAG TATGTACCCA GCTTCCCTCA GCACCACCCC CTCGCATAAC TTGGTTTCTT
         6310       6320       6330       6340       6350       6360       6370       6380       6390       6400
CTCTTCTTCC CCCAAGAGT GGACCAGGCC ATCTACGGCT GCCCCTCTCT CGAGCAGGTG GTCCCAGGTG GCCTCCCGTG CAGAAGGTAT GGGGGCAAG
         6410       6420       6430       6440       6450       6460       6470       6480       6490       6500
GCCTGTGATG GGCCTGAGAC CCCGGGAAGC GCCCTCTTAG ACTCGTAGCC CCTCCCTCTG TAGTGGAAGT AGCAGTGTGC ATGGTGGGAC CTAGTTGGAG
         6510       6520       6530       6540       6550       6560       6570       6580       6590       6600
GGGGCCGCA GAGGGCACGG TGTAGAATGT CGGTGCCTGG CCGGTGCCTGG GGCACAGTGG TGAGGGAGCG GCCTGGTAGA GCAGGTCTAC
         6610       6620       6630       6640       6650       6660       6670       6680       6690       6700
CAGCTCTGCC CCCAAGCTCA CCTGCTTCAA GAGGTTCCAT GTGGCCACCC CCCTTCCACC AGCACTCCCT CCGAGGGCTT CGGAGTCTGG
         6710       6720       6730       6740       6750       6760       6770       6780       6790       6800
TAGAGCCCCG CCTCCCACGA CAGGAACCCC CCTCTCCAGC TGCCCTTGCT CACAGGACAC CTGGGCAGTT GCTGGATCAG AGAGTCAGAG GGGGCTTCCT
         6810       6820       6830       6840       6850       6860       6870       6880       6890       6900
GCAGGAGCGG GGGCCATGAG ACCTCGGAGG GTGGACTGTG GTGGGTGAAG GGAGAAGGCA GCACATTCCA GGCCGGCAGGC AGCCGGGGCA AAGGCTTGGC
         6910       6920       6930       6940       6950       6960       6970       6980       6990       7000
AGTGGGATGG CAGGGAGCCT GACAAAGTGG AAAATGTGTG GGTTAAAGGA GGGAGGGCGG GGTCCTGGAA GACACTGACA TCCTCCTGCT ACGTGGGAGG
         7010       7020       7030       7040       7050       7060       7070       7080       7090       7100
AGACACAGGG CTCATCTGTA GCCATAGACA GACATGCCAA GGAAACGCGC AGGCCTGCCC GACTCTCCAG AAGGGAAATT GTCCCTGGCC CCAGCTCACC
         7110       7120       7130       7140       7150       7160       7170       7180       7190       7200
AAGCCTGGTC GGGCCAATTA GGGCCTAGTC TAGGGAACAG GTGAGCTGTT CCTTCCAGCT CACATGTTCA AATTTCCTCC AGCCCCAGCT CTGAGCAGCG
```

FIG. 1F

```
        7210          7220          7230          7240          7250          7260          7270          7280          7290          7300
AGCCGGGCTT  TGAGCGCCCT  CTACTGGCAG  GAAGCTCTGG  CGCTGGAAGC  ATGTTTAGAG  AGGGTCTGAG  GCTCGGTTCC  TAGAAACCTG  GAGGACCTGG 7310          7320          7330          7340          7350          7360          7370          7380          7390          7400
GCCTGGTGTC  CTCTGTGGTG  ATGGAGACAG  AGCTGGCGGG  AGCCATCGCT  TCCCTACCCT  GGGCCAACCA  GGGCACCACA  GACCCAGAGG  GAAGCCAAGG 7410          7420          7430          7440          7450          7460          7470          7480          7490          7500
TAGTGACGAT  CCCGGGACAG  TGGCCTGCTC  ACCCACAGAT  AGGGCGTTGG  GGTCCCAGCG  GATTCTGGGC  AGTGGAAGGC  AGGTGCGTCC  GTGTTCCTGG 7510          7520          7530          7540          7550          7560          7570          7580          7590          7600
CTTGACAGCA  CTTGCGAGTG  GGACTCCAGG  GACAGGAAG   GATTCACTTC  GGCTGGAGCA  GGAAGAGTGT  TTCAGAAAGG  AAGGGAGATG  CCAAAGTCCT 7610          7620          7630          7640          7650          7660          7670          7680          7690          7700
TAAATGCCAA  GTTTAGTCTC  TGGGTTTGAT  GCTCCAGGAA  GTTTGGAGAG  GCGGGTGGGA  GAGCAAGAGA  CGGGCGTGGT  GTGCAATGTG  ATGTCAATCT 7710          7720          7730          7740          7750          7760          7770          7780          7790          7800
ATCTAAAAAC  AGTTTGGCTT  CCAAGAAGGT  CTTAGCAGGG  CGCGGGGGTG  TCAGGGGTTA  CAGAAGTCAT  TTGAGATTAA  TCCCAGCAGA  TGTGTCATGT 7810          7820          7830          7840          7850          7860          7870          7880          7890          7900
CTCAGAGAGG  GACCAAGGGC  AGGGCTGATT  TGCAAGCTTG  GGATGTGCTG  TGTTTCCTTC  AGAAGGGTCC  CACCTCCCTG  GGCTCTTCGA  GGAGAGGGGC 7910          7920          7930          7940          7950          7960          7970          7980          7990          8000
TGTGTGATTT  GAGGCCAGAG  GGGCCTCTCC  CTCCCTCACA  TCTGAGCAGG  CGACAAGCTG  CCTGCCCTAG  AGCTGGCCCA  GGGCGGCTCG  GAAGCCTTTG 8010          8020          8030          8040          8050          8060          8070          8080          8090          8100
CTGGGCTCTT  CCCTGGGCAG  TGGGACCATG  ACAGACGAAA  GAACCTGTTT  CTCATCTCTC  CAAGCTGTGG  GCACCCCTGC  CGCTGCCCCT  GCCCCTGCCA 8110          8120          8130          8140          8150          8160          8170          8180          8190          8200
AGGGCTACAA  ACTTTTCCAG  CTCAAGCCCA  AATCTCCTCA  AGTGATGCCT  ATTGAAGAAT  TCCAAGGTAA  GAGGATGGAC  CTGGGGCCCC  ATCAGCCCTC 8210          8220          8230          8240          8250          8260          8270          8280          8290          8300
CCTGACACCT  GTTCCCCATC  CGCCGCTGGA  AAAAGACGGT  GCAGGATAGA  GGACCGATGC  CTGGCTCCGA  AAACCCTCCT  GGAGTAGCTG  GGTCAAGGTT 8310          8320          8330          8340          8350          8360          8370          8380          8390          8400
AAACTGAGTC  TCTCCTCCCT  ACAGGCCTCC  CTCCCCAAGG  GAGCTGGGAG  CAGGTATGAG  TCAGAAGCCA  AGTGGGCTAG  AGTGGGCAC   GCCACACAGC
```

FIG. IG

```
          8410       8420       8430       8440       8450       8460       8470       8480       8490       8500
AGGCAGAGCA GATGCCAGAA ATAGCCCATC CCGGCTTCCC TGGGAGGTGT GGCCCTGGGG CTTGGTTGTG TCTAAGCAGA ATCTGGACAC ACGGTCACCA
          8510       8520       8530       8540       8550       8560       8570       8580       8590       8600
TGCTGCTCTT GGACACTATA GGATGCCTCA TCTCCTCATT ATCTCTGGAG GGACAAAGTG AAGGGGGCAG GACTAGTGGA CAGTGGGATG CCCACCATCT
          8610       8620       8630       8640       8650       8660       8670       8680       8690       8700
CTCCTGGGCA CAGGCTGTTT CTCTAGTCTC CCAATGCCCT TGACCACTGG GTCAGTCCCT CATCCCATCA CAAAAGGGAA GCTGGGTCCT CTAGAGATAC
          8710       8720       8730       8740       8750       8760       8770       8780       8790       8800
ACAGATGGTG TTTCAAGAGG GTGGCCGTTG TCCTTCCTTG TTCGGGGGCA GCCACATTGG CTTTCTTGCT GGAGGGTGGG TGGGTGGGTG AGTACTGTGT
          8810       8820       8830       8840       8850       8860       8870       8880       8890       8900
CCCTTCGTAG AACATCAAGG ATGCCCCCCC ATTCTTAGGG ATGTGACCTT CCTCACCAAA TCCTCCATTG ACAATGTGGG ATTCACCTCC AATCCCCTGA
          8910       8920       8930       8940       8950       8960       8970       8980       8990       9000
GAGAGCCTGG CCCCAGGCAG TCACGGGCTT GTCTGGTCCT TGGAGCGGAG CTGGTTAGGC AGGGGTCAGC CTGAGAACCA CGTAGGGGTG GGGTGCAGGA
          9010       9020       9030       9040       9050       9060       9070       9080       9090       9100
GGGGCAGGA CATGGTGGTG GTGTGCCTTG GTATGAAACC ATGTGCTTCC AGGAGCAGCG AGTCAGAAGC CGGGCCAGGA CCAGGGGGAG GCATGCAGGT
          9110       9120       9130       9140       9150       9160       9170       9180       9190       9200
TCCCAGGGCT CCTGCTTTAA AGTGGCCACTC ACTCTTAGCA TCCTGCAAAT CAATCAAACT TGCACAAAGC TCAGGCTAAT AAGAAAGGGT CTGGCAGGTG
          9210       9220       9230       9240       9250       9260       9270       9280       9290       9300
GGCGTTTTCC TCCCAGCCAT CTTCCAAAGC AGCATGGGCA GGAGCTCCTG GCCCATTGCA TCTTGTCCAG CGTCCATCCA TGCATTCATC TACCCGAGGA
          9310       9320       9330       9340       9350       9360       9370       9380       9390       9400
TACCACGGCG AGCGCCGTGA ACCCAGGGCT CGCCTCCCCC AGTGCACAGC CAGGTGGCAT GACCCGTCCC TCCTTGCATG AATCACTTTC TAATCACCCC
          9410       9420       9430       9440       9450       9460       9470       9480       9490       9500
GGCATGTGGG CATTCCTTCA GCGAGCGCTT CGCCCTCCCC CCCAGCCAGG CATTAGCAGG AGCTGCCCAT GGCCCTGCCT GGTTCCCTGG GGACAGGCAG
          9510       9520       9530       9540       9550       9560       9570       9580       9590       9600
GTGGGAATCC TGGGCTAGCT ACTCAGGTTC TCCTCTGGGC TCAAAGCAGG GAGGCCTCTC TCTTCCTGAA TCCGATGGCA AGGGTGGGAG GCCTAGGGCA
```

FIG. 1H

```
          9610       9620       9630       9640       9650       9660       9670       9680       9690       9700
CCTTCCGGTA CCTTTTCCAA AGATGCCTTC CTCCTGCCCT GCATGACCTG GGGTGAGTCC TTCCTGCCCC TGTCCCTCAG TTTCCTGAAT GCTCGGCTGAC
          9710       9720       9730       9740       9750       9760       9770       9780       9790       9800
CATTGGTATT TCTCCCACTT GGCCGGCCCA GACTGCGAAT GCTACGGTCA CTCCAACCGC TGCAGCTACA TTGACTTCCT TGAATGTGGT GACCTGCGTC
          9810       9820       9830       9840       9850       9860       9870       9880       9890       9900
AGCTGCAAGC ACAACACGCG AGGTCAGCAC TGCCAGCACT GCCGGCTGGG CTACTACCGC AACGGCTCGG CACAACTGGA TGATGAGAAC GTCTGCATTG
          9910       9920       9930       9940       9950       9960       9970       9980       9990      10000
GTTGAGAGGG CACGGACACG GCACAGGGAA CTTGCTGGAA TGCGTGCAGG GTGCACTGCC CTGCGAGGTG GCCTCTGGGG GCCCCCTGCA TCAGAATCAC
         10010      10020      10030      10040      10050      10060      10070      10080      10090      10100
CTGGGAGAC TGTGGGAATT CTAACTCCAG GGCCCCTCTCC AGTTGAGCAT CTCTAAGGAC AGAAAGCTCC AGAAACTGCT CTATTAGTAA CCTACCCTTG
         10110      10120      10130      10140      10150      10160      10170      10180      10190      10200
CGGTTCTCCG GTAAGTTTTG CACTGGAGTT GCAAAACTTA CCAGTGGCCC TTCCCTCTCT GGGCAACTGG AGGGGACACT GACCCTTCTG GCTCAAAGAG
         10210      10220      10230      10240      10250      10260      10270      10280      10290      10300
CTGTGACTCT GGCAGGTGGC AGGCGACTCA TGGCAGAGGC CACTGAGCAT CTGTCTGGGG CTGGTGTGTG GGGGGTCCCC CTCCATAGCT CCTTTCCAGA
         10310      10320      10330      10340      10350      10360      10370      10380      10390      10400
AAGGTGGAGG AGCAGCCTAT CCCTCTCCT GCAGGGGGGC AGTTGGGGGC AAAAGATCGC CTTGCTGCGT GCATTGTGC AAGTCCCTTC CCGTTGCTGG
         10410      10420      10430      10440      10450      10460      10470      10480      10490      10500
GCCTCAGCTT CCTCATTCAT CAAATTGGGA GGCAGATCAG ATCAAAGGTT TTCAGCTCTT TTTTGTGGCT GAAGCTTTTC TTCAAATGCT TTACCAGCCC
         10510      10520      10530      10540      10550      10560      10570      10580      10590      10600
AGGTCCAGCT ATAAAGCTGC TCTTCACCCC TGGTGGGCAC CCAGTCTGCT TTCTTCCAAG TTGCTACTCA AGGACTGGCT TCTGGGTAGA GAAGGAAGTC
         10610      10620      10630      10640      10650      10660      10670      10680      10690      10700
CATCAGGGCC CTGGGCTGGG CAAAGACCCA AAGCCATGAC CGCCAACCAA ACGCACAGCT GGAATGGTTG CCCTGTCGTC AGTAGAGGCC AGGTCTCGGC
         10710      10720      10730      10740      10750      10760      10770      10780      10790      10800
CTCAGGGCT GTCCCCCAAC CCTGCCCAGC CAGGCCCTTG GGACACCATC ACCCATCCCC CACCCAGCAG GAGGCTCTGG CTGCCCAGAG GAGGGGCTCC
```

```
10810 10820 10830 10840 10850 10860 10870 10880 10890 10900
TGCAAAGCTG GAGCTGTCGG TCTGAATTCT GGCGGCCATG TCAGATAATT CCATCAACTC TAAGTGATCA AAGCCGCTGA CGTCACAGGG GGCCAGCTGC 10910 10920 10930 10940 10950 10960 10970 10980 10990 11000
AGGGACAGGG CAGGGCCTTT GGATCCAATT AGAGGTGCCC ACACCCTGGC ACCCTCCTCC TCTCCCTGCC TCTCCCTGGC TCCACCCCGA GAGCCAGCAC 11010 11020 11030 11040 11050 11060 11070 11080 11090 11100
TGAGCTGCAA GGTTTCTCAG GGTGGACGAT ATTCACCCTC TCCCACAGAG CCCCAAGGCA ACCAACTGGG CCCACCCGGG AGCAGGAATA GGCTGTTCCT 11110 11120 11130 11140 11150 11160 11170 11180 11190 11200
CCACGTCCCC TGCAAAGGAG CTATGGGAGG GGGCCACCCA CAACACAGCA GCCCCAGACA TGCTCAGTGG CCTCTGCTGA GTTTCTGCCA CTGTCGGAGT 11210 11220 11230 11240 11250 11260 11270 11280 11290 11300
CATAGCTCTT TGGAGATGGG AAGGACAGCG ACCCTCTAGT TGCCCAGAGA GGGGAAGGGG CTGACCAGGC CACACCAGTG CCAGGGCGGG GAAGGTGGGG 11310 11320 11330 11340 11350 11360 11370 11380 11390 11400
CTGGGACGTG TTTGATCCCA AGGAAGGAAG CCAGAGTCTT CTCTCCAGGC CTGGCCACCC TGGGAAGTCC CCACCTGCCC TCCAGCGCGG GGCTCACGTG 11410 11420 11430 11440 11450 11460 11470 11480 11490 11500
GACCCAGTGT GGGGAGCATC CCCTGGGGAG TGTGGAGATG CTCCCTGCGA GGCTGGGAGA GTGGGGTCC GAGCAAGACG GCGCCACAC GTAGCCCTGA 11510 11520 11530 11540 11550 11560 11570 11580 11590 11600
CCGCGCGCC GTGCCCGTGT CCGTCCAGAG TGTAACTGCA ACCAGATAGG CTCCGTGCAC GACCGGTGCA ACGAGACCGG CTTCTGCGAG TGCCGGCGAGG 11610 11620 11630 11640 11650 11660 11670 11680 11690 11700
GCGCGGCGCG CCCCAAGTGC GACGACTGC TCCCACGCAC TACTGGCGCA GGGCTGCTAC GTGAGTGCGC GCCGTCCCCG TGGCGGGCCT CGGAAAGGGG 11710 11720 11730 11740 11750 11760 11770 11780 11790 11800
AGGGCTAGA CCAGGCATGG CGGGCCTATGG GTGGCAAGCA CTAGCAAGCA GGGCAGGCCG GGAATGGTGG GCCTATGGCA GGGCAAGAGG 11810 11820 11830 11840 11850 11860 11870 11880 11890 11900
CGTGGGCGGG CCTCGGGAGA CGGGGCAGGC TGGGCCTAGT GAGACGGGCA AGGTTGGGAT AGTTGGCAGG GCCTGGGTGA GATGGGACCG 11910 11920 11930 11940 11950 11960 11970 11980 11990 12000
ACCCGGGATC GTGGACGGGA CTCTAGCGGAG ACGGAGCTGG CAGGTGGGCG GGGACAGGAT GCTGCTGAGG TCCGGGCAC GGGCCGAGGG GCGGGTCCAA
```

```
GAGCTCGGGG CGGGGCCTGA TGCGACCTGA GCACGGTGGT GCCTGGTGGG AACTACGAGA AAGACCGAGC TGGGGTTGGA AAGGTATTTG CGGGGACAGA
     12010      12020      12030      12040      12050      12060      12070      12080      12090      12100
GGGAGGGAGG CTGTCCAAGT CGGCGTTAGC CGGGGGCACA GGGTGAAAGG AGGCTCCAGG CGGCGTGGAC AGCACGTGCA CAGCTCTGGA GACTGCAGGC
     12110      12120      12130      12140      12150      12160      12170      12180      12190      12200
GCGTCTGAAG AACAGCACCG AGGCCAGTGG GGCGGGGAGA GAGGGGCAGC GGTGGAGGC ACCGGGGCC AGATCTCGCC CGGGGCCGT CACCCTCCGA
     12210      12220      12230      12240      12250      12260      12270      12280      12290      12300
GGGGGACGT TTCGCACCCA GCGCGCCTGG AGCCTCCTAC ATCCCCGGCC CAGACGGGCG CCCCGGGGTC TCGCACACCC TGTTCGAGAG CTCGGAGGTT
     12310      12320      12330      12340      12350      12360      12370      12380      12390      12400
GGCGGGGGGA CCGGGCCACC CCCCGGGGCT ACCCGTGCTG CCTGCAGCCA ACGTGTGCGA CGACGACCAG CTGCTGTGCC AGAACGGAGG CACCTGCCTG
     12410      12420      12430      12440      12450      12460      12470      12480      12490      12500
CAGAACCAGC GCTGCGCCTG CCCGCGCGGC TACACCGGGG TGCCTGCGA GCCAGCCCCG CTGCGACCC GCCGACGATG ACGGGCGTCTG GACTGCGACC
     12510      12520      12530      12540      12550      12560      12570      12580      12590      12600
GCGCGCCCGG GGCCGGCCCC CGCCCCGCCC ACCCTGCTCG GCTGCCTGCT GCTGTGGGG CCTGGCCCG CCTGGCCCGC TGAGCCCCGC CCGGAGGAGT
     12610      12620      12630      12640      12650      12660      12670      12680      12690      12700
CCCCGCACCG GAGGCGGGGG TCCGGGTCC GGCGGGCCGG CAGTCGAGGC CGGCGGTGAG AAGGGTGCGG CCGAGGTGC TCCCAGGTGC TACTCAGCAG
     12710      12720      12730      12740      12750      12760      12770      12780      12790      12800
GGCCCCCCC CCGGCCCGCG CTCCCGCCCG CACTGCCCCG AGGGGCGCAG TGGGACTCCG GTCCCGGCAG CCTGCGATTT GGTTTCGTTT
     12810      12820      12830      12840      12850      12860      12870      12880      12890      12900
TTCTTTTGTA TTATCCGCCG CCCAGTTCCT TTTTTGTCTT TCTCTCTCTC TTTTTTTTT TGGCGGTGAG CAGAGGGTCG GGAGAAACGC
     12910      12920      12930      12940      12950      12960      12970      12980      12990      13000
TGCTCGCCCC ACACCCGTCC TGCCTCCCAG CACACTTACA CACACGGGAC TGTGGCCGAC ACCCCTGGCC TGTGCCAGGC TCACGGGCGG CGGCGGACCC
     13010      13020      13030      13040      13050      13060      13070      13080      13090      13100
GAGCTGCAGT TGCCTACAAT TCCTAGCGCT GACTTGTCCT GTTTCTATTC TTATTTTCCT GCAACCCACC ACACCCCAGG CCTACGCAG GGCCCGGTGA
     13110      13120      13130      13140      13150      13160      13170      13180      13190      13200
```

FIG. IK

```
13210      13220      13230      13240      13250      13260      13270      13280      13290      13300
CCACGCAACT CACCCTCTGG GAGGAGGAGA GAAGCAAGGG GTGGGGGGCC CTGGAAATTC GCTTCTGTAG AGAATCTTTT TGTTTGTATT CACTGTCCTG 13310      13320      13330      13340      13350      13360      13370      13380      13390      13400
CAAGGGGAC  GGGCAGGACT GGTCAGCCGC GGGGGCCGAT GGTGGAGAAT CCGAGGAAGT AAAGAGGTTT GCTCACTGCT GCCTCCACGG CCTGTTTTCT 13410      13420      13430      13440      13450      13460      13470      13480      13490      13500
TTCTGTGTTG GGCACGGGTGG GCAGGTGTGG GGCTTACAGA GGAATCCACA ACACAGCCTT AAAGAAACGT TTCCTACTGG GGCCACCATT TCCCTGGGCC 13510      13520      13530      13540      13550      13560      13570      13580      13590      13600
TTTCTGTGGA TTCCAGCAGC AGTGCCCCCT CCCCGCAGGC TTGGCTGGCA GAGTTTTCCA CCCCGCGGCC AGGCTGCAGG TGCCCCACCT GTTAGGACCC 13610      13620      13630      13640      13650      13660      13670      13680      13690      13700
TCCCCACACT GAAAGGCTGC CTCCCTCCTT TCCCAAAAAA GAAATCCGGA GTGTATTGGC CCTTTTCTAC AAGAAGTCCA AGGGAAATGA CTCAGGGAGA 13710      13720      13730      13740      13750      13760      13770      13780      13790      13800
ATCCTAGCAG AGCTTGAATC CAATGCTCTG ATTTATACTG TGTCTCGGTG GCCACCTCCG ATGGATGTGT CATCTCAGAC CTGTTGCAGC CGGAGCCTCA 13810      13820      13830      13840      13850      13860      13870
AGTCCAATAT CAGATGAAGC TGAACCCACA ATGTCGGCCA CCGCCTCCTT CCGAGATTTC AGATGGCATG AATTC
```

METHOD OF PRODUCING A CELL CARRYING AN EXCESS OF MAMMALIAN CENTROMERES AND THE CELL LINE CARRYING AN EXCESS OF MAMMALIAN CENTROMERES

This application is a continuation of U.S. application Ser. No. 08/375,271, filed Jan. 19, 1995, now U.S. Pat. No. 5,712,134. The subject matter of U.S. application Ser. No. 08/375,271 is herein incorporated by reference. U.S. application Ser. No. 08/375,271 is a file wrapper continuation of U.S. application Ser. No. 08/080,097, filed Jun. 23, 1993, now abandoned, which in turn is a file wrapper continuation of U.S. application Ser. No. 07/892,487, filed Jun. 3, 1992, now abandoned, which in turn is a continuation of U.S. application Ser. No. 07/521,073, filed May 9, 1990 now abandoned.

BACKGROUND OF THE INVENTION

The centromere is a specialized region of the eukaryotic chromosome. It is the site of kinetochore formation, a structure which allows the precise segregation of chromosomes during cell division. In addition to this, a possible structural role in the higher-order organization of eukaryotic chromosomes has also been suggested (Hadlaczky (1985), Internatl. Rev., 94:57–76).

The isolation and cloning of centromeres is crucial, not only to understanding their molecular structure and function, but also for the construction of stable artificial chromosomes. Taking advantage of the existence of centromere-linked genes, functional centromeres of lower eukaryotes (yeast) have been successfully isolated (Blackburn, et al. (1984) Ann. Rev. Biochem., 53:163–194; Clarke, et al. (1985), Ann. Rev. Genet., 19:29–56). The combination of a functional centromere with telomeres, which stabilize the chromosome ends, permitted the construction of yeast artificial chromosomes (Murray, et al. (1983) Nature, 305:189–193; Burke, et al. (1987), Science, 236:806–812). This initiated a new era in the study of chromosome function and in genetic manipulation.

Higher eukaryotes (e.g., mammals), in contrast to yeast, contain repetitive DNA sequences which form a boundary at both sides of the centromere. This highly repetitive DNA interacting with certain proteins, especially in animal chromosomes, creates a genetically inactive zone (heterochromatin) around the centromere. This pericentric heterochromatin keeps any selectable marker gene at a considerable distance, and thus repetitive DNA prevents the isolation of centromeric sequences by chromosome "walking."

Thus there is a need in the art for methods of isolating higher eukaryotic centromeric DNA. Isolation of such DNA is necessary for construction of artificial mammalian chromosomes. Use of such chromosomes could overcome problems inherent in present techniques for introduction of genes to mammalian cells, including the concomitant creation of insertional mutations, size limitations on introduced DNA, and imperfect segregation of plasmid vectors.

SUMMARY OF THE INVENTION

It is an object of the present invention to provide a method for isolating centromeric DNA from a mammal.

It is another object of the invention to provide a DNA element which will insure faithful segregation of inserted DNA in meiosis and mitosis.

It is yet another object of the invention to provide a DNA element for formation of vectors to insert large amounts of DNA into mammalian cells.

It is still another object of the invention to provide a DNA element which binds mammalian centromere proteins.

These and other objects are provided by one or more of the embodiments described below.

In one embodiment a non-human cell line is provided that contains an excess of centromeres.

In another embodiment a nucleic acid probe is provided which hybridizes to a DNA molecule having the sequence shown in FIG. 1.

In yet another embodiment a method of isolating centromeric DNA from a mammal is provided comprising:

isolating metaphase chromosomes of a mammalian cell line;

fragmenting the chromosomes to form a suspension containing chromosome fragments;

incubating the suspension with human serum containing anti-centromere antibodies to bind chromosome fragments to the antibodies;

separating antibody-bound chromosome fragments from the suspension; and deproteinizing said bound fragments to provide a preparation of centromeric DNA.

In still another embodiment a method is provided of producing a cell carrying an excess of mammalian centromeres, comprising:

cotransfecting cells with: (1) DNA carrying mammalian centromeric DNA; and (2) DNA carrying a dominant selectable marker;

selecting cells which express the dominant selectable marker;

detecting cells which carry an excess of mammalian centromeres.

These and other embodiments will be described in more detail below. The present invention thus provides the art with methods to access and isolate the important centromeric DNA of mammalian cells. In particular, a human DNA fragment CM8 is provided which can be used to create artificial chromosomes for gene therapy.

BRIEF DESCRIPTION OF THE DRAWINGS

FIG. 1 provides the sequence of a 13,863 bp fragment of DNA identified in a λ Charon 4A human genomic library.

Lanes A and B: DNA isolated from chromosome fragments remaining unbound to anti-centromere Sepharose.

Lanes C and D: DNA isolated from chromosome fragments bound to anti-centromere Sepharose. Note the presence of a population of high molecular weight DNA fragments. Samples of lanes B and D were treated with 100 µg/ml RNase-A prior to electrophoresis.

Lane M: λ HindIII marker.

Figure 3:
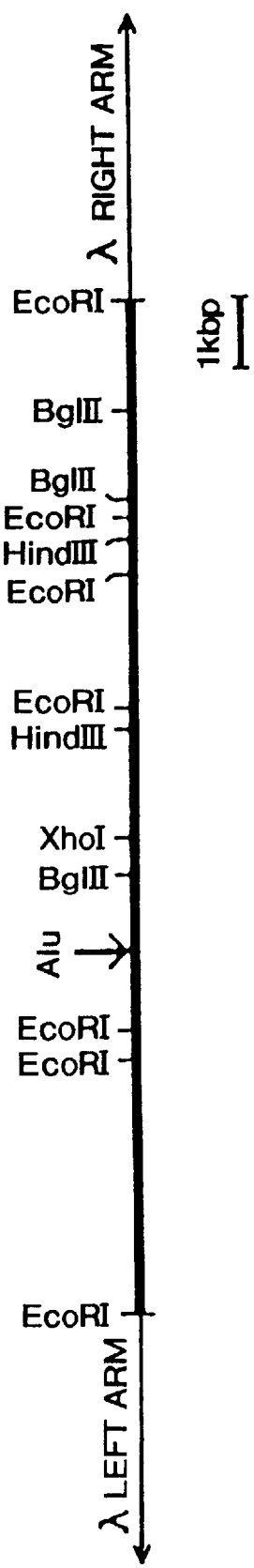

FIG. 3 shows a restriction map of the human genomic DNA insert of CM8 λ Charon 4A clone. The arrow shows the position of a 300 bp Alu repeat deficient in the flanking direct repeat sequences.

Figure 4A:
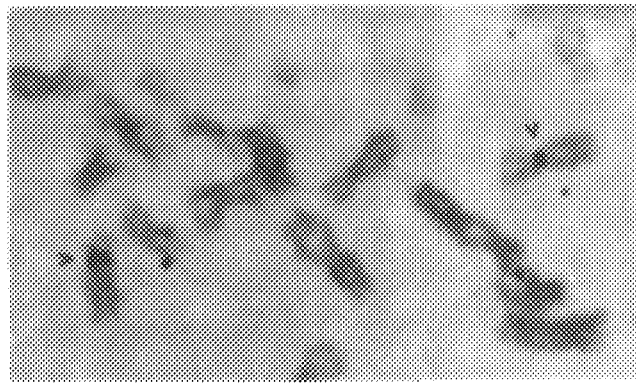

FIGS. 4A and B shows the results of in situ hybridization with $^3$H-thymidine labelled CM8 DNA to human metaphase chromosomes.

Panel A: Preferential localization of silver grains at the centromeres of human chromosomes (arrowheads).

Panel B: Diagram showing the distribution of silver grains (.) on 131 metacentric chromosomes. Numbers indicate the frequency of silver grain localization to certain regions of the chromosomes.

FIGS. 5A through H shows the detection of dicentric and minichromosome of the EC3/7 cells by indirect immunofluorescence (panels A and B) with anti-centromere antibodies, and by in situ hybridization with biotin labelled CM8 probes (panel C) and with a 1 kb SmaI/BgmI fragment of APH-II gene (panel D).

Panels E and F: DNA staining with Hoechst 33258;

Panels G and H: DNA staining with propidium iodide. Panels E–H correspond to A–D, respectively. Arrowheads point to dicentric and minichromosomes.

FIGS. 6A through F shows the duplication of the extra centromere in the EC3/7 cell line.

Panels A–C: In situ hybridization with biotin labelled CM8 probe.

Panels D–F: Corresponding DNA staining of A–C, respectively.

FIGS. 7A through F demonstrates the colocalization of the integrated DNA sequences with the centromere region detected by immunostaining with anti-centromere serum (Panels A and D) and subsequent in situ hybridization with biotin labelled CM8 (panel B) and APH-II probe (panel E) on the same metaphases of the EC3/7 cells.

Panels C and F: DNA staining.

DETAILED DESCRIPTION

It is the discovery of the present invention that a segment of human DNA can be isolated and introduced into mouse cells and results in a functional centromere. The functional centromeres containing DNA of the present invention are preferably linked to a dominant selectable marker. This can be a resistance marker, such as the aminoglycoside-3' phosphotransferase-II which provides resistance to G418 (Sigma). Other such markers known in the art may be used.

The method of isolating centromeric DNA of the present invention can be applied to any higher eukaryote, especially mammals. Preferably a human cell line will be employed. Metaphase chromosomes are isolated according to techniques known in the art. The chromosomes are then fragmented. Endonuclease digestion and mechanical shearing can be used to fragment the chromosomes. Desirably the majority of the fragments will be in the size range of less than 1 $\mu$m and some chromosomes will remain unbroken. Unbroken chromosomes can be readily removed from the preparation by centrifugation at about 1,500 g for about 10 minutes.

A human serum containing anti-centromere autoantibodies can be employed in the method of the invention. This is available from patients with CREST syndrome. Alternative sources of antibody may be used, such as monoclonal or animal derived polyclonal sera containing anti-centromere antibodies. The antibodies are incubated with the preparation of chromosome fragments under conditions where antibody-antigen complexes form and are stable. It is convenient if the antibodies are bound to a solid support. Preferably a support such as Protein-A Sepharose CL4B (Pharmacia) is used to facilitate separation of bound from unbound chromosomal fragments. However other methods to accomplish this goal can be used, as are known in the art, without employing an antibody bound to a solid support.

The DNA fragments comprising centromere DNA are liberated from the antibodies and centromeric proteins by a deproteinization treatment. Ultimately the DNA is purified from all proteins, by degrading the proteins and extracting them from the chromosome fragment preparation. Any such treatment known in the art may be used including but not limited to proteases and organic solvents such as proteinase K and phenol.

The centromeric DNA fragments can be used for any purpose or application known in the art. For example, they can be labelled and used as probes; they can be ligated to vectors to clone or all part of the sequences; and they can be used to purify centromeric proteins by attachment to a solid support.

In one particular embodiment of the invention the centromeric DNA fragments are used to probe a library of genomic DNA from humans or other mammals for clones which hybridize. Hybridizing clones can be analyzed for their ability to perform functions which centromeric DNA possesses. One such function is to bind to centromeric proteins. Another such function is to form a structure in cells which can be cytologically detected using appropriate immunostaining with anti-centromere antibodies which particularly stain centromeres.

According to another method of the present invention a cell carrying an excess of mammalian centromeres is formed. The cell may be human or other mammalian. The centromere may comprise DNA isolated from the same or a different mammalian species as the cell. The method involves cotransfection of a cell with two DNA molecules: one is a DNA carrying centromeric DNA; the other is a DNA carrying a dominant selectable marker. Preferably these two DNA molecules contain sequences which allow concatamer formation, for example phage DNAs such as $\lambda$ phage. The first DNA molecule may be isolated from a library of genomic DNA using, for example, as a probe the centromeric fragments taught above. Alternatively the first DNA molecule may result from cloning the centromeric fragments taught above into a phage, for example $\lambda$, after manipulations to create fragments of the appropriate sizes and termini. The second DNA molecule is readily within the reach of those of skill in the art, for example a$\lambda$ phage carrying a drug resistance marker.

It is believed to be desirable to employ $\lambda$ phage DNA because it concatemerizes, however the absolute necessity of this has not been determined. Further, even if this property is necessary, other viral DNAs or DNA constructs may be able to supply this function. Such other means of achieving concatemerization are also contemplated within this method.

After cotransfection, cells are selected which express the dominant selectable marker, for example by growth in amounts of G418 which are cytotoxic for the cells without the marker. This selected population of cells is further screened to detect cells with an excess of mammalian centromeres. This screening can be done by standard cytogenetic techniques, as well as by immunostaining with anti-centromere antibodies. Desirably the lambda, marker, and centromeric DNA (from the $\lambda$ clone) will all be localized at the site of the extra centromere. This can be determined by in situ hybridization studies, which are well known in the art.

One cell line made by the methods described above is EC3/7 which has been deposited at the European Collection of Animal Cell Cultures, Porton Down, U.K. under accession no. 90051001, under the conditions of the Budapest Treaty.

Figure 1C:
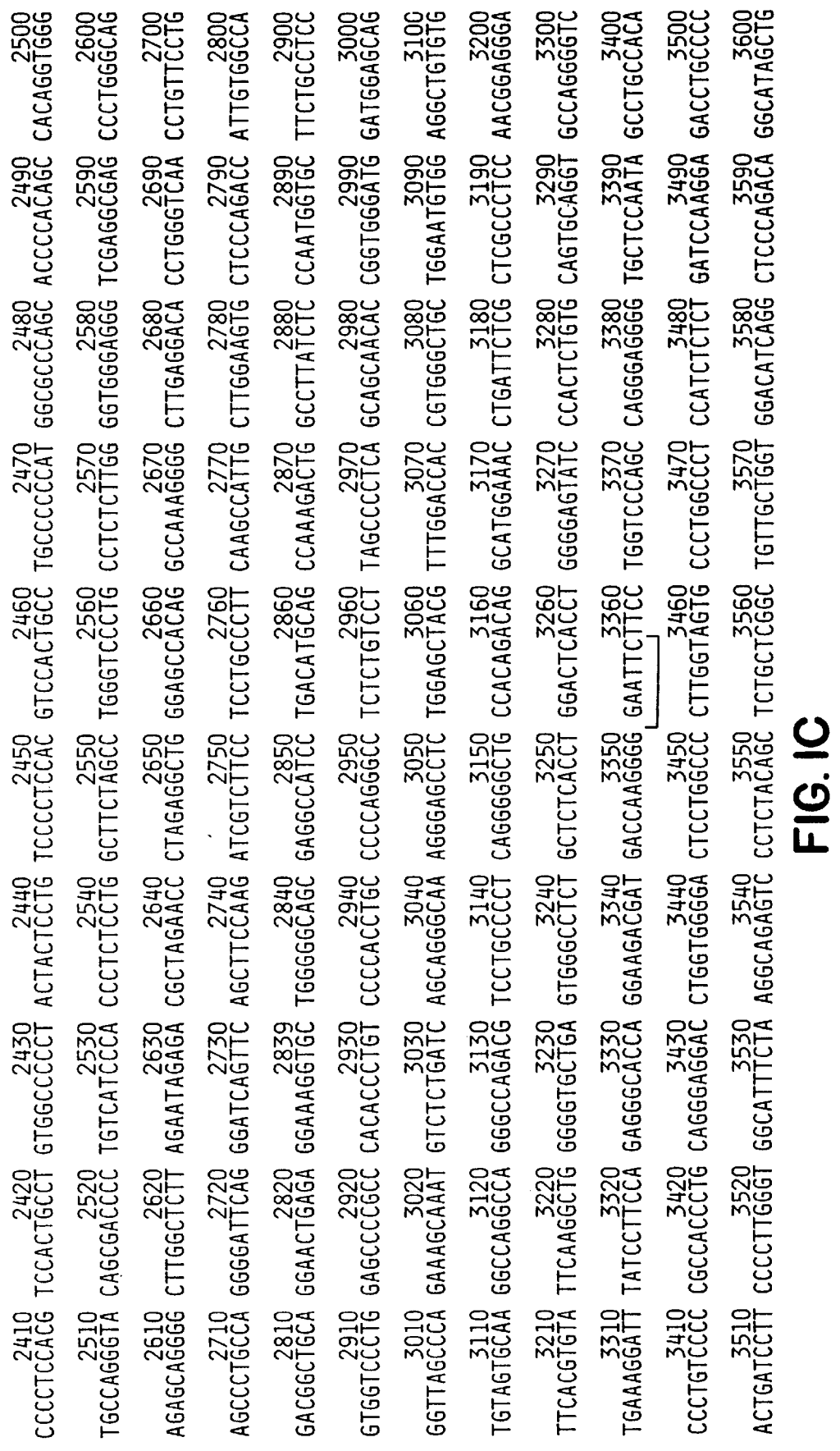

The sequence of the DNA insert in the lambda phage which was used to make the EC3/7 cell line, (referred to as CM8) was determined by standard techniques and is shown in FIG. 1. The sequence does not correspond to any in DNA sequence banks.

The present invention also contemplates nucleic acid probes, preferably of at least 10 nucleotides, which hybridize to a DNA molecule having the sequence shown in FIG. 1. One such molecule is CM8, the lambda phage clone from which the sequence was derived. Probes can be radiolabeled, biotin labeled or even unlabeled, for example, depending on the use for which they are desired.

The following examples do not limit the invention to the particular embodiments described, but are presented to particularly describe certain ways in which the invention may be practiced.

EXAMPLE 1

This example demonstrates the isolation of human DNA from centromeres.

Human colon carcinoma cell line (Colo 320) was grown as a suspension in RPMI medium supplemented with 10% foetal calf serum (FCS). Metaphase chromosomes of Colo 320 cells were isolated by our standard method (Hadlaczky, et al. (1982), Chromosomes, 86:643–659). Isolated metaphase chromosomes were resuspended in 1 ml of buffer (105 mM NaCl, 50 mM Tris-HCl pH 7.5, 10 mM $MgCl_2$, 5 mM 2-mercaptoethanol) at a concentration of 1 mg/ml DNA and digested with 500 u EcoRI restriction endonuclease for 1 h. The suspension was diluted with 4 ml of IPP buffer (500 mM NaCl, 10 mM Tris-HCl, 0.5% NP-40, pH 8.0) and sonicated for 5×50 s with an MSE 5–70 sonicator. This treatment resulted in a suspension containing chromosome fragments and a few (<1%) unbroken small chromosomes. The suspension was centrifuged at 1500 g for 10 min to remove unbroken chromosome fragments. The supernatant contained only small (<_1 μm) chromosome fragments as judged by light microscopy.

Two hundred fifty mg of Protein-A Sepharose CL4B (Pharmacia) was swollen in IPP buffer and incubated with 500 μl human anti-centromere serum LU851 (Hadlaczky, et al. (1989), Chromosoma, 97:282–288) diluted 20-fold with IPP buffer. Suspension of sonicated chromosome fragments (5 ml) was mixed with anti-centromere Sepharose (1 ml) and incubated at room temperature for 2 h with gentle rolling. After 3 subsequent washes with 25 ml IPP buffer the Sepharose was centrifuged at 200 g for 10 min.

Isolation of DNA from the immunoprecipitate was carried out by Proteinase-K treatment (Merck, 100 μg/ml) in 10 mM Tris-HCl, 2.5 mM EDTA, pH 8.0 containing 1% SDS, at 50° C. overnight, followed by repeated phenol extractions and precipitation with isopropanol. All general DNA manipulations were done according to (Maniatis, et al. (1982) Molecular Cloning—A Laboratory Manual (Cold Spring Harbor Laboratory, Cold Spring Harbor, N.Y.).

Figure 2:
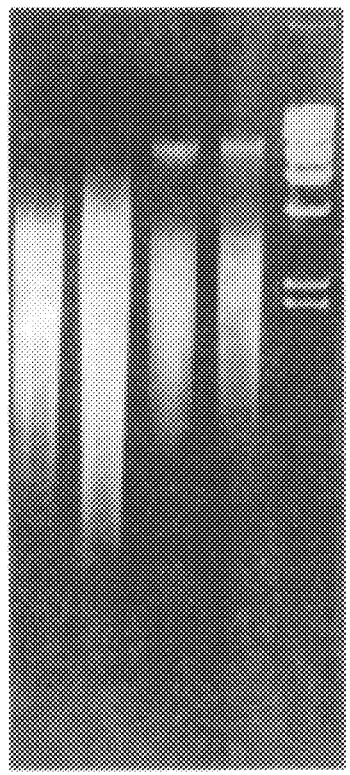
FIG. 2 shows the results of agarose gel electrophoresis of DNA fragments obtained by immunoprecipitation.

Results of electrophoresis of immunoprecipitated and supernatant DNA are shown in FIG. 2. The bulk of DNA from chromosome fragments which did not bind to the anti-centromere Sepharose (supernatant) ranged from several hundred base pairs to 5 kb (FIG. 2, lanes A and B), while DNA from chromosome fragments which bound to the anti-centromere Sepharose contained an additional population of high molecular weight (9–20 kb) fragments (FIG. 2, lanes C and D). This distribution of fragments sizes is consistent with the notion that the centromeric DNA is in the structurally most stable region of mammalian chromosomes (Hadlaczky, et al. (1981), Chromosoma, 81:557–567), thus rendering this DNA relatively resistant to enzymatic digestion and mechanical shearing.

EXAMPLE 2

This example demonstrates the use of the high molecular weight immunoprecipitated DNA as a hybridization probe to screen a genomic DNA library.

The high molecular weight DNA was isolated from the agarose gel described in Example 1, by electroelution, labelled with $^{32}$P-dATP by random oligonucleotide priming (Feinberg, et al. (1983), Anal. Biochem., 132:6–13) and used as a probe for screening a λ Charon 4A human genomic library (Maniatis, et al. (1978), Cell, 15: 687–701). A hybridizing clone (CM8) was obtained which contains a 14 kb human DNA insert. The restriction map of this insert for some restriction endonucleases is shown in FIG. 3. Southern hybridization of parts of the 14 kb insert to human lymphocytic genomic DNA indicates that the 14 kb insert represents a continuous piece of DNA in the genome and is not the ligation product of a number of fragments.

EXAMPLE 3

This example demonstrates that the copy number of the 14 kb insert of clone CM8 is consistent with it being present on each chromosome in the human genome.

Southern blotting experiments were performed in which a single copy DNA probe (XV2C) (Estivill, et al. (1987), Nature, 326:840–845) and the central XhoI-EcoRI fragment of the CM8 insert (FIG. 2) simultaneously hybridized with serial dilutions of human peripheral lymphocyte DNA. The probes were labelled by random oligonucleotide priming (Feinberg, et al. (1983), Anal. Biochem., 132:6–13). By comparing the signal of the CM8 probe to the known single copy probe, the copy number of CM8 was estimated to be 16–32 per haploid genome.

EXAMPLE 4

This example shows the use of the CM8 DNA as a probe to human metaphase chromosomes.

Figure 4B:
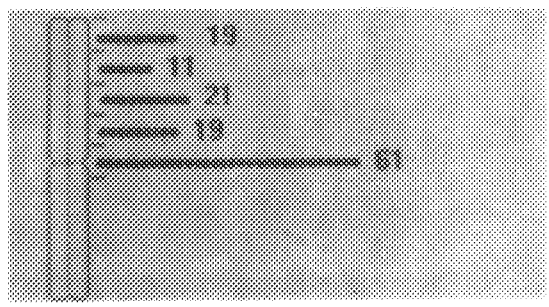

Radioactive in situ hybridization with $^3$H-thymidine labelled CM8 DNA to human (Colo 320) metaphase chromosomes was performed according to the method of Pinkel, et al. (1986), Proc. Natl. Acad. Sci. U.S.A., 83:2934–2938. A preferential centromeric localization of silver grains was observed (FIG. 4).

In non-radioactive in situ hybridization according to the method of (Graham, et al. (1973), Virology, 52:456–467), using biotin-labelled subfragments or the whole CM8 insert it was not possible to detect a positive hybridization signal by our standard method. Furthermore, using a hybridization method which is suitable for single copy gene detection with a biotin-labelled probe (Lawrence, et al. (1988), Cell, 52:51–61), apart from the typical R-band like Alu hybridization pattern (Korenberg, et al. (1988), Cell, 53:391–400), no specific hybridization signal was detected on any of the chromosomes with the whole 14 kb CM8 insert. Possible explanations for this negative result are that these sequences are virtually inaccessible to the hybridization probe, due to their compact packing in the midst of the centromere structure, and that the biotin system is less sensitive than the radioactive one.

EXAMPLE 5

This example discloses the sequence of the human CMB clone.

The sequence of the human genomic insert of λ CM8 was determined using the dideoxy method (Sanger, et al. 91980), J. Mol. Biol., 143:161–178; Biggin, et al. (1983), Proc. Natl. Acad. Sci. U.S.A., 80:3963–3965). See FIG. 1.

The sequence of the 13,863 bp human CM8 clone was compared with a complete nucleic acid data bank (MicroGenie, Beckman) and showed no homology to any known sequence. However, a 300 bp Alu repeat deficient in the flanking direct repeat sequences was found in the 2.5 kb EcoRI-XhoI fragment (FIG. 3), which explains the Alu type in situ hybridization pattern.

EXAMPLE 6

This example demonstrates the use of the CM8 DNA to form centromeres in mammalian cells.

In order to detect any in vivo centromere function of the CM8 DNA, it was introduced with the selectable APH-II gene into mouse LMTK⁻fibroblast cells. The mouse fibroblast cells were maintained as a monolayer in F12 medium supplemented with 10% FCS. The calcium phosphate method (Harper, et al. (1981), Chromosoma, 83:431–439) was used to transfect the cells with 20 $\mu$g $\lambda$ CM8 and 20 $\mu$g $\lambda$ gtWESneo DNA per Petri dish (80 mm). A 2 minute glycerol shock was used. The $\lambda$gt WESneo was made by cloning the pAG60 plasmid (Colbere-Garapin, et al. (1981), J. Mol. Biol., 150:1–14) into a $\lambda$ gtWES (Leder, et al. (1977), Science, 196:175–177) bacteriophage vector.

The whole $\lambda$ CM8 and $\lambda$ gt WESneo constructions were used for transfections for two reasons. First, to separate the marker gene from the CM8 sequences, in order to avoid inactivating the APH-II gene, a process which may occur during centromere formation. Second, $\lambda$ DNA is capable of forming long tandem arrays of DNA molecules by concatamerization. Concatamerization was postulated as being necessary to form centromeres since, in S. pombe 4 to 15 copies of conserved sequence motifs form centromeres (Chikashige, et al. (1989), Cell, 57:739–751). Considering these two facts a multiplication of the putative centromeric DNA by concatamerization might increase the chance of centromere formation.

Transformed cells were selected on growth medium containing 400 $\mu$g/ml G418 (Genticin, Sigma). Individual G418 resistant clones were analyzed. The presence of human sequences in the transformed clones was monitored using Southern blots probed with subfragments of the CM8 insert. Screening for excess centromeres was achieved by indirect immunofluorescence using human anti-centromere serum LU851 (Hadlaczky, et al. (1989), Chromosoma, 97:282–288). The chromosomal localization of "foreign" DNA sequences was determined by in situ hybridization with biotin labelled probes.

Figure 5A:
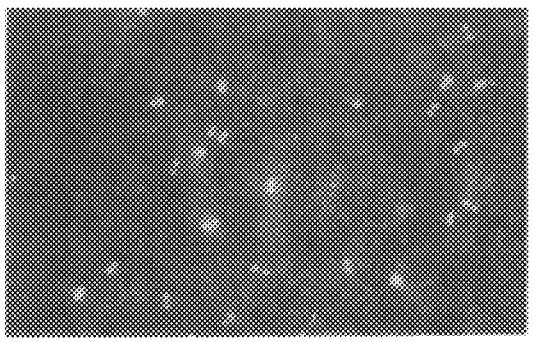
Figure 5B:
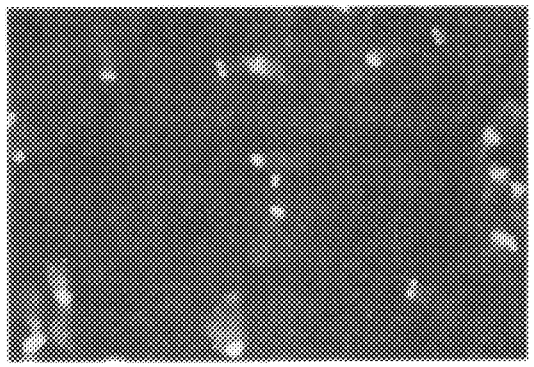
Figure 5C:
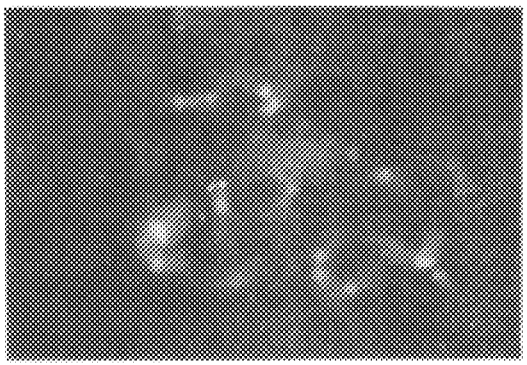

Eight transformed clones have been analyzed. All of the clones contained human DNA sequences integrated into mouse chromosomes. However, only two clones (EC5/6 and EC3/7) showed the regular presence of dicentric chromosomes. Individual cells of clone EC5/6 carrying di-, tri-, and multicentromeric chromosomes exhibited extreme instability. In more than 60% of the cells of this cell line the chromosomal localization of the integrated DNA sequences varied from cell to cell. Due to this instability, clone EC5/6 was deemed to be unsuitable. However, cells of clone EC3/7 were stable, carrying either a dicentric (85%) or a minichromosome (10%). Centromeres of dicentric chromosomes and minichromosomes were indistinguishable from the normal mouse centromeres by immunostaining with anti-centromere antibodies (FIGS. 5A and B).

EXAMPLE 7

This example shows that the newly introduced DNA in the EC3/7 cell line contributes to centromere formation.

In situ hybridization with biotin labelled CM8, APH-II gene, and $\lambda$ phage DNA were carried out. Chromosomes were counterstained with propidium iodide (Pinkel, et al. (1986), Proc. Natl. Acad. Sci. U.S.A., 83:2934–2938) for in situ hybridization experiments while in indirect immunofluorescence with DNA binding dye, Hoechst 33258 used. All observations and microphotography were made by using an Olympus AHBS Vanox microscope. Forte 400 Professional black and white, and Fujicolor 400 Super HG colour film were used for photographs.

Figure 5D:
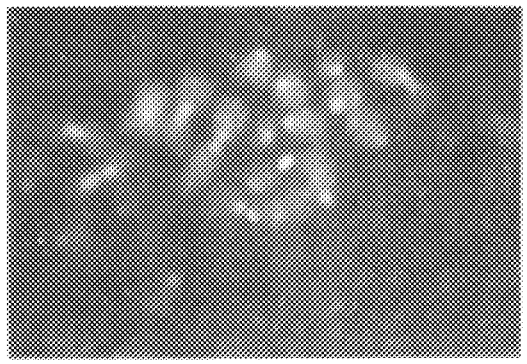
Figure 5E:
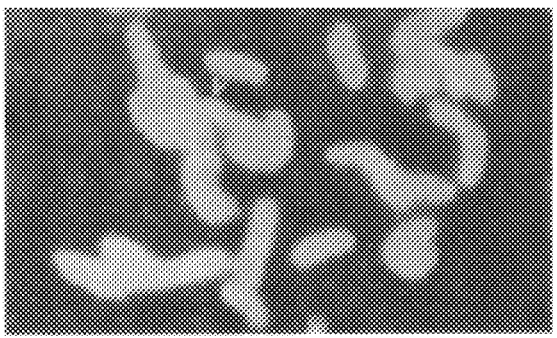
Figure 5F:
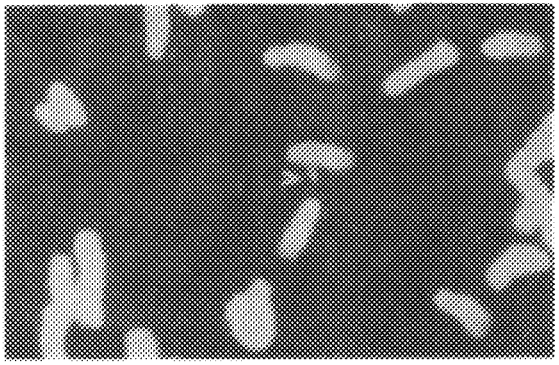
Figure 5G:
Figure 5H:
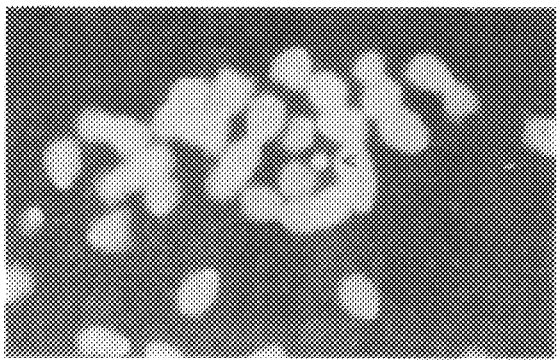
Figure 6A:
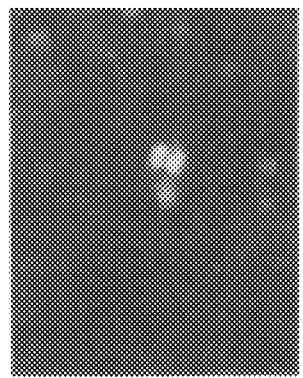
Figure 6B:
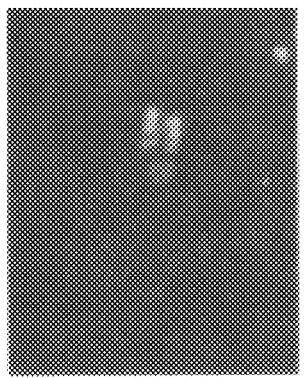
Figure 6C:
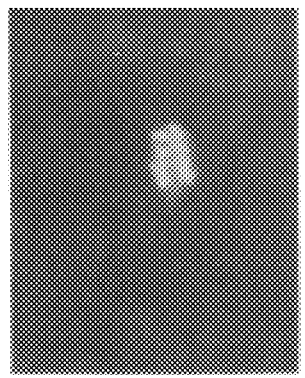
Figure 6D:
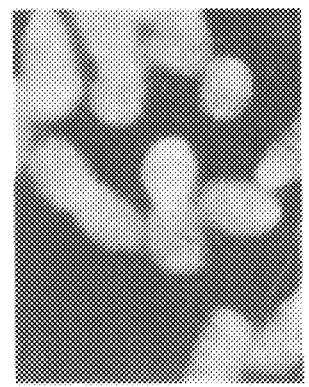
Figure 6E:
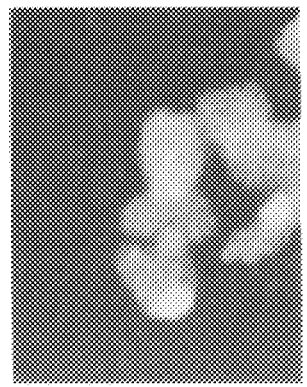
Figure 6F:
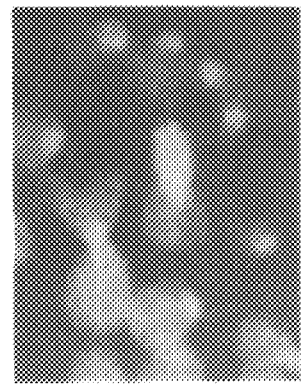

Without exception these three probes hybridized onto the same spots: either on the distal centromere of the dicentric chromosome (FIG. 5C) or on the centromere of the minichromosome (FIG. 5D). In less than 5% of the EC3/7 cells an alternative localization of the hybridization signal was found. These included cells with more than one integration site, cells without a detectable signal, or cells where the hybridization was found on chromosomes other than that identified as the dicentric chromosome.

Figure 7A:
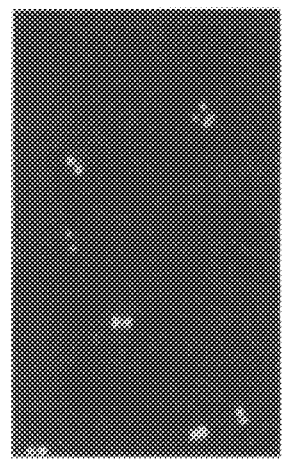
Figure 7B:
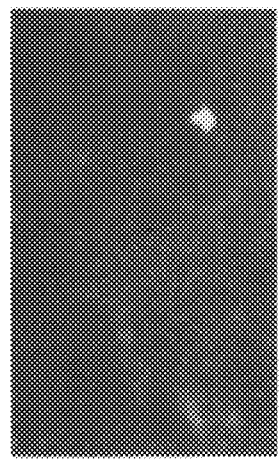
Figure 7C:
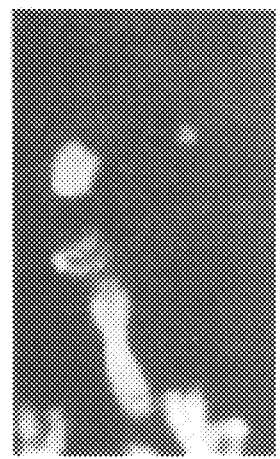
Figure 7D:
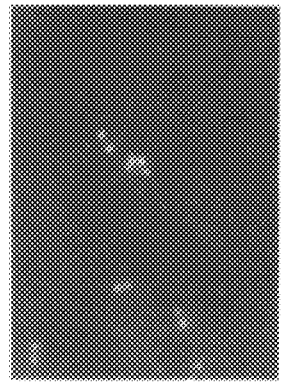
Figure 7E:
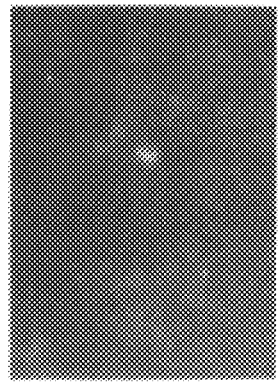
Figure 7F:
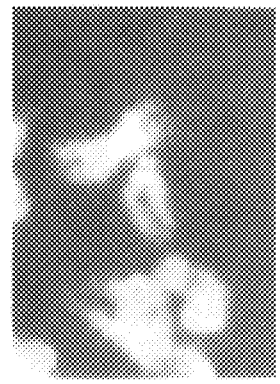

In less than 0.5% of the cells a tandem array of the hybridization signal was observed on the dicentric chromosomes (FIGS. 6A–C), suggesting that the additional centromere was capable of autonomous "duplication." At least some of these duplicated centromeres appeared to be functional. This was indicated by the existence of a minichromosome with double centromeres. Both centromeres of this minichromosome showed positive immunostaining with anti-centromere antibodies (FIG. 7A). Minichromosomes carrying double centromeres might be breakage products of multicentromeric chromosomes.

Indirect immunofluorescence of mouse metaphase cells was performed as described by Hadlaczky, et al. (1989), Chromosoma, 97:282–288. When indirect immunofluorescence and in situ hybridization were performed on the same metaphases, mitotic cells were resuspended in a glycine-hexylene glycol buffer (Hadlaczky, et al. (1989), Chromosoma, 97:282–288), swollen at 37° C. for 10 min followed by cytocentrifugation and fixation with cold (−20° C.) methanol. After the standard immunostaining (Hadlaczky, et al. (1989), Chromosoma, 97:282–288) metaphases were photographed, then coverslips were washed off with phosphate buffered saline and slides were fixed in ice-cold methanol-acetic acid, air-dried and used for in situ hybridization.

To demonstrate the integration of the human CM8 clone sequence and the APH-II gene in the centromere region, immunostaining of centromeres with anti-centromere antibodies followed by in situ hybridization with CM8 and APH-II probes was carried out on the same metaphase plates of EC3/7 cells. The in situ hybridization signals with both biotin-labelled CM8 and APH-II probes showed a colocalization with the immunostained centromeric region of the chromosomes carrying additional centromeres (FIG. 7).

EXAMPLE 8

This example describes the stability of the EC3/7 cell line.

Forty-six independent subclones derived from a single cell were isolated and analyzed. Each of the subclones carried the dicentric chromosome. The percentage of minichromosome-containing cells varied between 2% and 30% in different subclones. We were unable to isolate a subclone which carried the additional centromere exclusively in a minichromosome. This result suggested that the minichromosomes were unstable and they can be regarded as the products of regular breakages of the dicentric chromosomes.

A preliminary analysis by immunostaining of EC3/7 cells (103 metaphases) cultured for 46 days in non-elective medium showed that 80.6% of the cells contained either a dicentric (60.2%) or a minichromosome (20.4%). Subsequent in situ hybridization with biotin labelled probes proved the presence of the "foreign", DNA in the additional centromere. These results indicate that no serious loss or inactivation of the additional centromeres had occurred during this period of culture under non-selective conditions.

EXAMPLE 9

This example shows that the CM8 insert concatamerized to form the functioning centromere of cell line EC3/7.

DNA of the EC3/7 cell line and human lymphocyte DNA were digested with restriction endonucleases and probed with subfragments of the CM8 insert in a Southern hybridization experiment. Comparing the intensity of the hybridization signal with EC3/7 DNA to that with the human DNA, the minimum number of integrated human sequences in the additional centromere was estimated to be $\geq 30$. The copy number of CM8 in human lymphocytic DNA was determined as described above in Example 3.

---

I claim:

1. A non-human mammalian cell line, comprising cells that contain an excess of centromeres, wherein the cells comprise human DNA that hybridizes under selective conditions to the sequences of nucleotides set forth in FIG. 1.

2. The cell line of claim 1, wherein the human DNA comprises the sequence of nucleotides set forth in FIG. 1.

3. A rodent cell line, comprising cells that contain an excess of centromeres, wherein the cells comprise human DNA that hybridizes under selective conditions to the sequences of nucleotides set forth in FIG. 1.

4. The rodent cell line of claim 3, wherein the cells are mouse cells.

5. The cell line of claim 4, wherein the cells comprise the sequence of nucleotides set forth in FIG. 1.

6. A rodent cell line, comprising cells that contain an excess of centromeres, wherein:

the cells comprise human DNA that hybridizes under selective conditions to the sequences of nucleotides set forth in FIG. 1; and human autoantibodies isolated from CREST syndrome patients bind to one or more chromosomes in cells in the cell line.

7. A cell that is selected from cells that have all of the identifying characteristics of the cells deposited at the European Collection of Animal Cell Cultures (ECACC) under accession no. 90051001.

8. A cell line having all of the identifying characteristics of the cells deposited at the European Collection of Animal Cell Cultures (ECACC) under accession no. 90051001.

9. A rodent cell line produced by a method, comprising:

(a) cotransfecting cells with a DNA fragment comprising human DNA and a DNA fragment encoding a dominant selectable marker, wherein the human DNA fragment comprises the sequence of nucleotides set forth in FIG. 1;

(b) growing the cells and selecting cells that express the dominant selectable marker;

(c) detecting among the cells that express the dominant selectable marker those cells with an excess of mammalian centromeres.

10. A rodent cell line produced by a method comprising:

(a) cotransfecting cells with a DNA fragment comprising human DNA and a DNA fragment encoding a dominant selectable marker, wherein the human DNA fragment comprises the sequence of nucleotides set forth in FIG. 1;

(b) growing the cells under selective conditions and selecting cells that express the dominant selectable marker;

(c) detecting among the cells that express the dominant selectable marker those cells with an excess of mammalian centromeres that include a chromosome with two centromeres.

11. A rodent cell line produced by a method, comprising:

(a) cotransfecting cells with a DNA fragment comprising human DNA and a DNA fragment encoding a dominant selectable marker, wherein the human DNA fragment comprises the sequence of nucleotides set forth in FIG. 1;

(b) growing the cells under selective conditions and selecting cells that express the dominant selectable marker;

(c) detecting among the cells that express the dominant selectable marker those cells with an excess of mammalian centromeres that include a minichromosome, wherein the minichromosome is smallest chromosome in the cell.

* * * * *

UNITED STATES PATENT AND TRADEMARK OFFICE
CERTIFICATE OF CORRECTION

PATENT NO. : 5,891,691                                        Page 1 of 2
DATED      : April 6, 1999
INVENTOR(S): Hadlaczky It is certified that error appears in the above-identified patent and that said Letters Patent is hereby corrected as shown below:

IN THE TITLE PAGES:

In item [63] entitled Related U.S. Application Data, "Ser No. 80,097" should read — 080,097 —

In Item [56] entitled Other Publications, add — Rogers, et al., "[26] Gene transfer in plants: Production of transformed plants using Ti plasmid vectors", *Methods for Plant Molecular Biology*, Weissbach et al., eds., Academic Press, N.Y. Section VIII, pp.423-436, (1988). —

In Item [56] entitled Other Publications, add — Rommens, et al., identification of the cystic fibrosis gene: chromosome walking and jumping, *Science* 245:1059-1065 (1989). —

In Item [56] entitled Other Publications, add — Rosenfeld, et al., *In vivo* transfer of the human cystic fibrosis transmembrane conductance regulator gene to the airway epithelium, *Cell* 68:143-155 (1992). —

In Item [56] entitled Other Publications, add — Sambrook, et al., *Molecular Cloning: A Laboratory Manual, Volume 1*. 2nd Ed., Cold Spring Harbor Laboratory Press, Section 2.18 (1989). —

In Item [56] entitled Other Publications, add — Sanes, et al., Use of recombinant retrovirus to study post-implantation cell lineage in mouse embryos, *EMBO J.* 5(12):3133-3142 (1986). —

In Item [56] entitled Other Publications, add — Sang, et al., "Transgenic chickens - methods and potential applications", *TIBTECH* 12:415-420 (1994). —

In Item [56] entitled Other Publications, add — Sanger, et al., Cloning in single-stranded bacteriophage as an aid to rapid DNA sequencing, *J. Mol. Biol.* 143:161-178 (1980). —

In Item [56] entitled Other Publications, add — Saxon, et al., Selective transfer of individual human chromosomes to recipient cells, *Mol. Cell. Biol.* 1:140-146 (1985). —

In Item [56] entitled Other Publications, add — Schedl, et al., A method for the generation of YAC trangenic mice by pronuclear microinjection, *Nucl. Acids Res.* 21:4783-4787 (1993). —

In Item [56] entitled Other Publications, add — Scientists report a major step in realizing the commercial potential of engineered artificial chromosomes in significant life sciences sectors, including gene therapy, *Chromos Molecular Systems - News Release* (May 29, 1996)

UNITED STATES PATENT AND TRADEMARK OFFICE
CERTIFICATE OF CORRECTION

PATENT NO. : 5,891,691
DATED : April 6, 1999
INVENTOR(S) : Hadlaczky

It is certified that error appears in the above-identified patent and that said Letters Patent is hereby corrected as shown below:

In Item [56] entitled Other Publications, add — Selig, *et al.*, Regulation of mouse satellite DNA replication time, *EMBO J.* 7:419-426 (1988). —

In Item [56] entitled Other Publications, add — Smith, *et al.*, Distinctive chromosomal structures are formed very early in the amplification of CAD genes in Syrian hamster cells, *Cell* 63:1219-1227 (1990). —

In Item [56] entitled Other Publications, add — Solus, *et al.*, "Characterization of single-copy Probe from Vicinity of Centromere of Human Chromosome 1", *Som. Cell & Mol. Gen.*, 14(4):381-391 (1988). —;

In Item [56] entitled Other Publications, add — Sugden *et al.*, A vector that replicates as a plasmid and can be efficiently selected in B-lymphoblasts transformed by Epstein-Barr virus, *Mol. Cell. Biol.* 5:410-413 (1985). —;

In Item [56] entitled Other Publications, add — Sumner, Scanning electron microscopy of mammalian chromosomes from prophase to telophase. *Chromosoma* 100:410-418 (1991). —;

And in Item [57] entitled Abstract, after "a dominante marker gene are able to" replace "form" with — generate —.

Column 6, line 64 replace "CMB" with —CM8—.

Signed and Sealed this

Fifteenth Day of February, 2000

Attest:

Attesting Officer

Q. TODD DICKINSON

*Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13875 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GAATTCATGC  CATCTGAAAT  CTCGGAAGGA  GGCGGTGGCC  GACATTGTGG  GTTCAGCTTC    60
ATCTGATATT  GGACTTGAGG  CTCCGGCTGC  AACAGGTCTG  AGATGACACA  TCCATCGGAG   120
GTGGCCACCG  AGACACAGTA  TAAATCAGAG  CATTGGATTC  AAGCTCTGCT  AGGATTCTCC   180
CTGAGTCATT  TCCCTTGGAC  TTCTTGTAGA  AAAGGGCCAA  TACACTCCGG  ATTTCTTTTT   240
TGGGAAAGGA  GGGAGGCAGC  CTTTCAGTGT  GGGGAGGGTC  CTAACAGGTG  GGGCACCTGC   300
AGCCTGGCCG  CGGGGTGGAA  AACTCTGCCA  GCCAAGCCTG  CGGGGAGGGG  GCACTGCTGC   360
TGGAATCCAC  AGAAAGGCCC  AGGGAAATGG  TGGCCCCAGT  AGGAAACGTT  TCTTTAAGGC   420
TGTGTTGTGG  ATTCCTCTGT  AAGCCCCACA  CCTGCCCACC  GTGCCCAACA  CAGAAAGAAA   480
ACAGGCCGTG  GAGGCAGCAG  TGAGCAAACC  TCTTTACTTC  CTCGGATTCT  CCACCATCGG   540
CCCCCGCGGC  TGACCAGTCC  TGCCCGTCCC  CCTTGCAGGA  CAGTGAATAC  AAACAAAAAG   600
ATTCTCTACA  GAAGCGAATT  TCCAGGGCCC  CCCACCCCTT  GCTTCTCTCC  TCCTCCCCAG   660
AGGTGAGTTG  CGTGGTCACC  GGGCCCTGCG  GTAGGCCTGG  GGTGTGGTGG  GTTGCAGGAA   720
AATAAGAATA  GAAACAGGAC  AAGTCAGCGC  TAGGAATTGT  AGGCAACTGC  AGCTCGGGTC   780
CGCCGCCGCC  CGTGAGCCTG  GCACAGGCCA  GGGGTGTCGG  CCACAGTCCC  GTGTGTGTAA   840
GTGTGCTGGG  AGGCAGGACG  GGTGTGGGGC  GAGCAGCGTT  TCTCCCGACC  CTCTGCTCAC   900
CGCCAGAAAA  AAAAAAAAAA  AAAGAGAGAG  AGAGAAAGAC  AAAAAAGGAA  CTGGGCGGCG   960
GATAATACAA  AAGAAAAACG  AAACCAAATC  GCAGGCTGCG  GGGACCGGAG  TCCCAAGGCG  1020
```

```
CCCCTGCTGC GGGGGGAGGG CAGTGCGGGC GGGAGCGCGG GCCGGGCGGG GGGCCCTGCT    1080
GAGTAGCACC TGGGAGCACC TCGGGCCGCA CCCTTCTCAC CGCCGGCCTC GACTGCCGGC    1140
CCGCCGGACC CGGGACCCCG GCCTCCGGTG CGGGGACTCC TCCGGGCGGG GCTCAGCGGC    1200
CCAGGCGGCG GCCAGCCCCA GCAGCAGCAG GCAGCCGAGC AGGGTGGGCG GGGCGCGGGG    1260
CGGCCCCGGG CGCGCGGTCG CAGTCCAGAC GCCGTCATCG TCGGCGGGGT CGCAGCGGGG    1320
CTGGCTCGCA GCGCACGCCG GTGTAGCCGC GCGGGCAGGC GCAGCGCTGG TTCTGCAGGC    1380
AGGTGCCTCC GTTCTGGCAC AGCAGCTGGT CGTCGTCGCA CACGTTGGCT GCAGGAGGGG    1440
GCGGTCAGCA CGGGGGGTGG CCCGGTCCCC CCGCCAACCT CCGAGCTCTC GAACAGGGTG    1500
TGCGAGACCC CGGGGGCGCC GTCTGGGCCG GGGATGTAGG AGGCTCCAGG CGCGCTGGGT    1560
GCGAAACGTC CCCCCTCGGA GGGTGACGGC GCCCGGGCGA GATCTGGCCC CCGGTGCCTC    1620
CCACCGCTGC CCCTCTCTCC CCGCCCCACT GGCCTCGGTG CTGTTCTTCA GACGCGCCTG    1680
CAGTCTCCAG AGCTGTGCAC GTGCTGTTCC ACGCGCCTGG AGCCTCCTTT CACCCTGTGC    1740
CCGCGGCTAA CGCCGACTTG GACAGCCTCC CTCCCTCTGT CCCCGCAAAT ACCTTTCCAA    1800
CCCCAGCTCG GTCTTTCTCG TAGTTCCCAC CAGGCACCAC CGTGCTCAGG TCGCATCAGG    1860
CCCCGCCCCG AGCTCTTGGA CCCGCCCCTC GGCCCGTGCC CCGGACCTCA GCAGCATCCT    1920
GTCCCCGCCC ACCTGCCAGC TCCGTCTCGC TAGAGTCCCG TCCACGATCC CGGGTCGGTC    1980
CCATCTCACC AGGCCCCTGC CAACTATCCC AACCTTGCCC GTCTCACTAG GCCCACCATT    2040
GCCCGGCCTG CCCCGTCTCG CGAGGCCCCG CCACGCCTCT TGCCCTGCCA TAGGCCCACC    2100
ATTCCCGGCC TGCCCTGCTT GCTAGGCCAT GCCACGCCTG CCCTGCCATA GGCCGCCATG    2160
CCTGGTCTAG CCCCTCCCCT TTCCGAGGCC CGCCACGGGG ACGGCGCGCA CTCACGTAGC    2220
AGCCCTGCGC CAGTAGTGCG TGGGAGGCAG TCGTCGCACT TGGGGCGCGC CGCGCCCTCG    2280
CGGCACTCGC AGAAGCCGGT CTCGTTGCAC CGGTCGTGCA CGGAGCCTAT CTGGTTGCAG    2340
TTACACTCTG GACGGACACG GGCACGGGCG CGCGGTCAGG GCTACGTGTG GGCGCCGTCT    2400
TGCTCGGACC CCCACTCTCC CGGCCTCGCA GGGAGCATCT CCACACTCCC CAGGGGATGC    2460
TCCCCACACT GGGTCCACGT GAGCCCGCGG CTGGACGGCA GGTGGGGACT TCCCAGGGTG    2520
GCCAGGCCTG GAGAGAAGAC TCTGGCTTCC TTCCTTGGGA TCAAACACGT CCCAGCCCCA    2580
CCTTCCCCGC CCTGGCACTG GTGTGGCCTG GTCAGCCCCT TCCCCTCTCT GGGCAACTAG    2640
AGGGTCGCTG TCCTTCCCAT CTCCAAAGAG CTATGACTCC GACAGTGGCA GAAACTCAGC    2700
AGAGGCCACT GAGCATGTCT GGGGCTGCTG TGTTGTGGGT GGCCCCCCTC CATAGCTCCT    2760
TTGCAGGGGA CGTGGAGGAA CAGCCTATTC CTGCTCCCGG GTGGGCCAG  TTGGTTGCCT    2820
TGGGGCTCTG TGGGAGAGGG TGAATATCGT CCACCCTGAG AAACCTTGCA GCTCAGTGCT    2880
GGCTCTCGGG GTGGAGGCAG GGAGAGCCAG GGAGAGGAGG AGGGTGCCAG GGTGTGGGCA    2940
CCTCTAATTG GATCCAAAGG CCCTGCCCTG TCCTGCAGC  TGGCCCCCTG TGACGTCAGC    3000
GGCTTTGATC ACTTAGAGTT GATGGAATTA TCTGACATGG CCGCCAGAAT TCAGACCGAC    3060
AGCTCCAGCT TTGCAGGAGC CCCTCCTCTG GGCAGCCAGA GCCTCCTGCT GGGTGGGGA    3120
TGGGTGATGG TGTCCCAAGG GCCTGGCTGG GCAGGGTTGG GGGACAGCCC CTGAGGCCGA    3180
GACCTGGCCT CTACTGACGA CAGGGCAACC ATTCCAGCTG TGCGTTTGGT TGGCGGTCAT    3240
GGCTTTGGGT CTTTGCCCAG CCCAGGGCCC TGATGGACTT CCTTCTCTAC CCAGAAGCCA    3300
GTCCTTGAGT AGCAACTTGG AAGAAAGCAG ACTGGGTGCC CACCAGGGGT GAAGAGCAGC    3360
TTTATAGCTG GACCTGGGCT GGTAAAGCAT TTGAAGAAAA GCTTCAGCCA CAAAAAAGAG    3420
```

```
CTGAAAACCT TTGATCTGAT CTGCCTCCCA ATTTGATGAA TGAGGAAGCT GAGGCCCAGC    3480
AACGGGAAGG GACTTGCACA AATGCACGCA GCAAGGCGAT CTTTTGCCCC CAACTGGGCC    3540
CCTGCAGGAG GAGGGATAGG CTGCTCCTCC ACCTTTCTGG AAAGGAGCTA TGGAGGGGGA    3600
CCCCCCACAC ACCAGCCCCA GACAGATGCT CAGTGGCCTC TGCCATGAGT CGCCTGCCAC    3660
CTGCCAGAGT CACAGCTCTT TGAGCCAGAA GGGTCAGTGT CCCCTCCAGT TGCCCAGAGA    3720
GGGAAGGGCC ACTGGTAAGT TTTGCAACTC CAGTGCAAAA CTTACCGGAG AACCGCAAGG    3780
GTAGGTTACT AATAGAGCAG TTTCTGGAGC TTTCTGTCCT TAGAGATGCT CAACTGGAGA    3840
GGGCCCTGGA GTTAGAATTC CCACAGTCTC CCCAGGTGAT TCTGATGCAG GGGGCCCCCA    3900
GAGGCCACCT CGCAGGGCAG TGCACCCTGC ACGCATTCCA GCAAGTTCCC TGTGCCGTGT    3960
CCGTGCCCTC TCAACCAATG CAGACGTTCT CATCATCCAG TTGTGCCGAG CCGTTGCGGT    4020
AGTAGCCCAG CCGGCAGTGC TGGCAGTGCT GACCTCGCGT GTTGTGCTTG CAGCTGACGC    4080
AGGTCACCAC ATTCAAGGAA GTCAATGTAG CTGCAGCGGT TGGAGTGACC GTAGCATTCG    4140
CAGTCTGGGC CGGCCAAGTG GGAGAAATAC CAATGGTCAG CGAGCATTCA GGAAACTGAG    4200
GGACAGGGCG AGGAAGGACT CACCCCAGGT CATGCAGGGC AGGAGGAAGG CATCTTTGGA    4260
AAAGGTACCG GAAGGTGCCC TAGGCCTCCC ACCCTTGCCA TCGGATTCAG GAAGAGAGAG    4320
GCCTCCCTGC TTTGAGCCCA GAGGAGAACC TGAGTAGCTA GCCCAGGATT CCCACCTGCC    4380
TGTCCCCAGG GAACCAGGCA GGGCCATGGG CAGCTCCTGC TAATGCCTGG CTGGGCACCA    4440
GGGCCAAGCG CTCGCTGAAG GAATGCCCAC ATGCCGGGGT GATTAGAAAG TGATTCATGC    4500
AAGGAGGGAC GGGTCATGCC ACCTGGCTGT GCACTGGGGG AGGCGACGCC TGGGTTCACG    4560
GCGCTCGCCG TGGTATCCTC GGGTAGATGA ATGCATGGAT GGACGCTGGA CAAGATGCAA    4620
TGGGCCAGGA GCTCCTGCCC ATGCTGCTTT GGAAGATGGC TGGGAGGAAA ACGCCCACCT    4680
GCCAGACCCT TTCTTATTAG CCTGAGCTTT GTGCAAGTTT GATTGATTTG CAGGATGCTA    4740
AGAGTGAGTG CCACTTTAAA GCAGGAGCCC TGGGAACCTG CATGCCTCCC CCTGGTCCTG    4800
GCCCGGCTTC TGACTCGCTG CTCCTGGAAG CACATGGTTT CATACCAAGG ACCACCACCA    4860
CCATGTCCTG CCGCCTCCTG CACCCCACCC CTACGTGGTT CTCAGGCTGA CCCCTGCCTA    4920
ACCAGCTCCG CTCCAAGGAC CAGACAAGCC CGTGACTGCC TGGGGCCAGG CTCTCTCAGG    4980
GGATTGGAGG TGAATCCCAC ATTGTCAATG GAGGATTTGG TGAGGAAGGT CACATCCCTA    5040
AGAATGGGGG GGCATCCTTG ATGTTCTACG AAGGGACACA GTACTCACCC ACCCACCCAC    5100
CCTCCAGCAA GAAAGCCAAT GTGGCTGCCC CCGAACAAGG AAGGACAACG GCCACCCTCT    5160
TGAAACACCA TCTGTGTATC TCTAGAGGAC CCAGCTTCCC TTTTGTGATG GGATGAGGGA    5220
CTGACCCAGT GGTCAAGGGC ATTGGGAGAC TAGAGAAACA GCCTGTGCCC AGGAGAGATG    5280
GTGGGCATCC CACTGTCCAC TAGTCCTGCC CCCTTCACTT TGTCCCTCCA GAGATAATGA    5340
GGAGATGAGG CATCCTATAG TGTCCAAGAG CAGCATGGTG ACCGTGTGTC CAGATTCTGC    5400
TTAGACACAA CCAAGCCCCA GGGCACACC TCCCAGGGAA GCCGGGATGG CTATTTCTG    5460
GCATCTGCTC TGCCTGCTGT GTGGCCTAGC CCACTGTGCC CAAGTTGGCT TCTGACTCAT    5520
ACCTGCTCCC AGCTCCCTTG GGGAGGGAGG CCTGTAGGGA GGAGAGACTC AGTTTAACCT    5580
TGACCCAGCT ACTCCAGGAG GGTTTTCGGA GCCAGGCATC GGTCCTCTAT CCTGCACCGT    5640
CTTTTTCCAG CGGCGGATGG GGAACAGGTG TCAGGGAGGG CTGATGGGGC CCCAGGTCCA    5700
TCCTCTTACC TTGGAATTCT TCAATAGGCA TCACTTGAGG AGATTTGGGC TTGAGCTGGA    5760
AAAGTTTGTA GCCCTTGGCA GGGGCAGGGG CAGCGGCAGG GGTGCCCACA GCTTGGAGAG    5820
```

```
ATGAGAAACA GGTTCTTTCG TCTGTCATGG TCCCACTGCC CAGGGAAGAG CCCAGCAAAG    5880
GCTTCCGAGC CGCCCTGGGC CAGCTCTAGG GCAGGCAGCT TGTCGCCTGC TCAGATGTGA    5940
GGGAGGGAGA GGCCCCTCTG GCCTCAAATC ACACAGCCCC TCTCCTCGAA GAGCCCAGGG    6000
AGGTGGGACC CTTCTGAAGG AAACACAGCA CATCCCAAGC TTGCAAATCA GCCCTGCCCT    6060
TGGTCCCTCT CTGAGACATG ACACATCTGC TGGGATTAAT CTCAAATGAC TTCTGTAACC    6120
CCTGACACCC CCGCGCCCTG CTAAGACCTT CTTGGAAGCC AAACTGTTTT TAGATAGATT    6180
GACATCACAT TGCACACCAC GCCCGTCTCT TGCTCTCCCC ACCGCCTCTC CAAACTTCCT    6240
GGAGCATCAA ACCCAGAGAC TAAACTTGGC ATTTAAGGAC TTTGGCATCT CCCTTCCTTT    6300
CTGAAACACT CTTCCTGCTC CAGCCGAAGT GAATCCTTCG CTGTCCCTGG AGTCCCACTC    6360
GCAAGTGCTG TCAAGCCAGG AACACGGACG CACCTGCCTT CCACTGCCCA GAATCCGCTG    6420
GGACCCCAAC GCCCTATCTG TGGGTGAGCA GGCCACTGTC CCGGGATCGT CACTACCTTG    6480
GCTTCCCTCT GGGTCTGTGG TGCCCTGGTT GGCCCAGGGT AGGGAAGCGA TGGCTCCCGC    6540
CAGCTCTGTC TCCATCACCA CAGAGGACAC CAGGCCCAGG TCCTCCAGGT TTCTAGGAAC    6600
CGAGCCTCAG ACCCTCTCTA AACATGCTTC CAGCGCCAGA GCTTCCTGCC AGTAGAGGGC    6660
GCTCAAAGCC CGGCTCGCTG CTCAGAGCTG GGGCTGGAGG AAATTTGAAC ATGTGAGCTG    6720
GAAGGAACAG CTCACCTGTT CCCTAGACTA GGCCCTAATT GGCCCGACCA GGCTTGGTGA    6780
GCTGGGGCCA GGGACAATTT CCCTTCTGGA GAGTCGGGCA GGCCTGCGCG TTTCCTTGGC    6840
ATGTCTGTCT ATGGCTACAG ATGAGCCCTG TGTCTCCTCC CACGTAGCAG GAGGATGTCA    6900
GTGTCTTCCA GGACCCCGCC CTCCCTCCTT TAACCCACAC ATTTTCCACT TTGTCAGGCT    6960
CCCTGCCATC CCACTGCCAA GCCTTTGCCC CGGCTGCCTG CGGCCTGGAA TGTGCTGCCT    7020
TCTCCCTTCA CCCACCACAG TCCACCCTCC GAGGTCTCAT GGCCCCGCT CCTGCAGGAA    7080
GCCCCCTCTG ACTCTCTGAT CCAGCAACTG CCCAGGTGTC CTGTGAGCAA GGGCAGCTGG    7140
AGAGGGGGT TCCTGTCGTG GGAGGCGGGG CTCTACCAGA CTCCGAAGCC CTCGGAGGGA    7200
GTGCTGGTGG AAGGGCTTGG CGTGGGGGTG GCCACATGGA ACCTCTTGAA GCAGGTGAGC    7260
TTGGGGGCAG AGCTGGTAGA CCTGCTCTAC CAGGCCGCTC CCTCACCACT GTGCCCTAGA    7320
GCTCCCCAGG CACCGACATT CTACACCGTG CCCTCAGTTG GTTCCTGCGG CCCCCCTCCA    7380
ACTAGGTCCC ACCATGCACA CTGCTACTTC CACTACAGAG GGAGGGGCTA CGAGTCTAAG    7440
AGGGCGCTTC CCGGGGTCTC AGGCCCATCA CAGGCCTTGC CCCCCATACC TTCTGCACGG    7500
GAGGCCACCT GGGACCACCT GCTCGAGAGA GGGGCAGCCG TAGATGGCCT GGTCCACTCT    7560
TGGGGGGAAG AAGAGAAGAA ACCAAGTTAT GCGAGGGGGT GGTGCTGAGG GAAGCTGGGT    7620
ACATACTGAG GCATCACAGC CCCGCTACCC ACAGGCCCCT TAGAAGCAGC AGCACTATAA    7680
GGAGAGGCTC TGTCTACATG GCCAAAGGAA TTGGGTCCAA ATCTACTACA TAGGCAGCAT    7740
CTACACTATT TAGCCTGTGG AGGGCACATG CAGACTTAAA GCCCGATAGA TGAGAGGTGA    7800
ACCCATCGCC TGAGAATCTG CATACTTCTT CAGCGAGACC CTTCTACACT CCCTGTGCCC    7860
GTCCCCGTTC TGACTGAAGG ACAGAGCTAC GACCAGGTCC CGCCTCTGGG CCCAGACCTC    7920
TCTGAGCTGA TCTCTCTGGC TACATGGCTG CGAAGTGGGA CATCTCTTCC GGCCAAGATC    7980
TTACATGTGT CCAGAAGTGT CCTGGAAGGT GTCCTTCCTG TCCAGCCGCA ATCCAGGGAC    8040
CGGAGCCTTC CCCAGCATCT GACCTGCTTC CCTGATCACT GCCCTTCTAC CTTCCTGACC    8100
CCTGGCCTGG CCCATTTTCA CCAGGGACCC CAGCATGAAC CAGTGACACA ACGCTCAGCC    8160
CGTAGACTAA CGGGACACAC AGCCAGCAAG GCAGGCAGGC AGGGCTGGCA AAGAACTGCC    8220
```

```
TGTGCCAAAT TTCAAAGGAC AACCAGAGGA CAGGGGAGCG CTGCTGTTTT CGCTTCTTGA    8280
AGGGATTATA CACAACGGTG GCTGTGGGGA AGAAAGGAAA GCTACCAGCT AACAAGTGCG    8340
AAGACTTCCA GCTGGGAGCG GGGAGCTTTG GACACTGAAT TGACTTTAAT TATGATGTTC    8400
AGTGGGAAGA TGAGCGCCAG GCCCAAATTG CAGGCTTAAT TAGAGCCATG AGAAAGCCAG    8460
CCCTGAAGGC ATTTGCTTCA GAGCCTGTCT CCCTCCATCC TCCGTGCCCA GCCCAGGAAA    8520
GGATTAGTGT CTCCAGCGCG TTTTCCGCGC CGCAGCGCTG TCCTCCAGAC AGCTTGACAT    8580
TGGCAGGCGG GAGAAACATC TGGCCCAGGA GTTCAGAGGC CAGCTGGAC TCTGTTCAAA     8640
GAGCCCGAAG CACCTGTTGG GAGGCACTCG GGGGTATTCA GGATCTTTCA GGGACCAGGG    8700
TCTTGGGGAG GGAGGGAGTC CTGGCTTTGG CTGCCCAGGG ACACACTCAG GTGTGTGGGA    8760
AGCAAGTTCT CGCCATGGCC TGTGTGCTGT GCCAAGGCCC CATGGAAGCC CGGTCTGCTC    8820
CTTTGGAACT GGGAAGCCCT GCAAGCCAGG CCTTGGAGAC AGCACTACTT GGCCGGGTGC    8880
GGTGGCTCAC GCCTGGAATC CCAGCACTTT GGGAGGCTGA GGCGGGTGGA TCACTTGAGG    8940
TCAGGAGTTC AACACCAGCC TGACCAACAT GGTGAAACCC TGTCTCTCTA AAAAGACAAA    9000
AAGTAGCTGA ACATGGTGAC AGGTGCCTGT AATCCCAGCT ACTCGGGAGG CTGAGGCAGG    9060
AGAATTGCTT GAACCTGGGG GGGCGGAGGT TGCAGTGAGC TGAGATTGCT CCATTGCACT    9120
CCAGCCTCAG CGACAAGAGC GAAACTCCAT CTCAAAAAAA AAAAAAAAAA GATAGCTCTA    9180
CCTCATAGCC CCTGGAGGCC TCAGGACAAT AGCTTTGGGT GGCTGAGTTG GCGAGCCCTG    9240
AGTTCAAATC CTGCCCGTGC CTCTCCATAA TTCTGAGACC TTGAGCAGCT GCCCCTTTTT    9300
TCTTCTGAAA CAGCTTGATT GAGGTGTAAT TTTACATATC ATAAAATCCA GCTGCTTCTT    9360
CCTAAGCCTC GATCCCCTCA CCTGTGGGAC TAGGAAAATA ACAGCCTCCA TCTCACGGAG    9420
CTGTGAGCCC AGAATACAAT GATATGATGA TACAATCATA CGAGCACAGC CCAGGAGAAC    9480
TCACCCTCAG CTACTGCAAT GATCGTTTTC ATTAATGGGG GCTCTGGACA GGGGCTTCAG    9540
TTGCTGAAGA GGAGGGAGGA GCCCCTAGAT GTGGCTGTAG GGGCCACTGG CTGTCACATT    9600
GGAGCCACCT CCTCCCCTAA TGTCCTGCTT CTTGATACAG GGCTAGGTGC AGAGCAGCAC    9660
TGTCTTGCCG AGAGGGTGTG CCTTCTGCTC ACTGAGGGTC CTGGGGACCC TCAACTCCCC    9720
TGCATTTCCC ACTCTGGCCT CTGACTTTTC CTCTTTAATT CCCAACTTGC ACAATCTGCC    9780
CAGCCTCCCA CGGCTGGCCC TGGCACCAAG TCAGAAGCAG CTCTGCAAAT GGATTCCTCT    9840
GTGTGTGTGT GTGTGTACAT GTGCGTGTGC ATGCCTGTGT GTGTGCATGC ATGTGTGTGT    9900
GTGTGTGCAT GTGTGCACTT GCACATGTGA TATGGAGAGT ATCTGGCCTC CCAGCCAAAC    9960
CCCTGTTTGG AGACAGGCAC AGCACCCACC ACCACTGTTT TTGCTTCTGT CTGCCCACCA   10020
CAGGCTCATC AGCAAAGCAC AGGTCCCTTG TGGCTGGGCC AACCTATGTT TGAAGTCCAG   10080
AATTCTCAGA GTGACCCATG TCTTCCACCC CAAAGAGGAT TCCTGGGTCA GGAGGCTTCC   10140
CGGAAATCCT CCAATCTTTT GGCTAGAAAA TGCCTCCTGT AAATGCTCTG CAGAAAAGGA   10200
AGGATGTAGA AAGAGGTGGG GTGTGCTGCC CAGGGAGCT GCTCTGGATG GCCTAGGAAG    10260
GAGGAGGTCT TCTCTCAGCT ATGCCTGTCT GGGAGCCTGA TGTCCACCAG CAACAGCCGA   10320
GCAGAGCTGT AGAGGGACTC TGCCTTAGAA ATGCCACCCA AGGGGAAGGA TCAGTGGGGC   10380
AGGTCTCCTT GGATCAGAGA GATGGAGGGC CAGGGCACTA CCAAGGGGCC AGGAGTCCCC   10440
ACCAGGTCCT CCCTGCAGGG TGGCGGGGGA CAGGGTGTGG CAGGCTATTG GAGCACCCCT   10500
CCCTGGCTGG GACCAGGAAG AATTCCCCCT TGGTCATCGT CTTCCTGGTG CCCTCTGGAA   10560
GGATAAATCC TTTCAGACCC CTGGCACCTG CACTGCACAG AGTGGGATAC TCCCCAGGTG   10620
```

```
AGTCCAGGTG AGAGCAGAGG CCCACTCAGC ACCCCCAGCC TTGAATACAC GTGAATCCCT    10680
CCGTTGGAGG GCGAGCGAGA ATCAGGTTTC CATGCCTGTC TGTGGCAGCC CCCTGAGGGG    10740
CAGGACGTCT GGCCCTGGCC TGGCCTTGCA CTACACACAC AGCCTCCACA TTCCAGCAGC    10800
CCACGGTGGT CCAAACGTAG CTCCAGAGGC TCCCTTTGCC CTGCTGATCA GAGACATTTG    10860
CTTTCTGGGC TAACCCTGCT CCATCCATCC CACCGGTGTT GCTGCTGAGG GGCTAAGGAC    10920
AGAGAGGCCC TGGGGGCAGG TGGGACAGG GTGTGGGCGG GGCTCCAGGG ACCACGGAGG    10980
CAGAAGCACC ATTGGGAGAT AAGGCCAGTC TTTGGCTGCA TGTCAGGATG GCCTCGCTGC    11040
CCCCAGCACC TTTCCTCTCA GTTCCTGCAG CCGTCTGGCC ACAATGGTCT GGGAGCACTT    11100
CCAAGCAATG GCTTGAAGGG CAGGAGGAAG ACGATCTTGG AAGCTGAACT GATCCCTGAA    11160
TCCCCTGGCA GGGCTCAGGA ACAGGTTGAC CCAGGTGTCC TCAAGCCCCT TTGGCCTGTG    11220
GCTCCAGCC TCTAGGGTTC TAGCGTCTCT ATTCTAAGAG CCAAGCCCCT GCTCTCTGCC    11280
CAGGGCTCGC CTCGACCCTC CCACCCCAAG AGAGGCAGGG ACCCAGGCTA GAAGCCAGGA    11340
GAGGGTGGGA TGACAGGGGT CGCTGTACCC TGGCACCCAC CTGTGGCTGT GGGGTGCTGG    11400
GCGCCATGGG GGGCAGGCAG TGGACGTGGA GGGGACAGGA GTAGTAGGGG CCACAGGCA    11460
GTGGACGTGG AGGGGACAGG AGTAGTAGGG GGCCCTGTCA TGGCTCTCGT GGCCGCAAGT    11520
GCCACAGGGC CTTTGGGGTC GGGGTCTTTC TGGGACCTGC TGATGCCTGG TGAGAGATGG    11580
GAAAAGCAAG AGAGGGTTGG GGGTTGGCCG GGGTGGGGAC ACCACAGAGA AGCAACTTAG    11640
CACGGCTGTG CAGACCAGCG TCCCTGCAGG GTCCAGCTTC TTTCTGGCGC CCTCTCGGCT    11700
CACTGGCTTC CCAGCCAGGG GCCCCCTGGG TCCGGGAGGG ACAACTTGGG TGGGATGTGG    11760
GGCCCCACAG AGCCCTGGTG GAGGGTGACG GCCCCAGAAG CATCTCTGAG ATTTGGGGTC    11820
TGCTCCCGGC TGGCTCTTTG ACATTGGCCA GTCCTCTCCT GCTGCCTCGC AGAGCAGATG    11880
GCGACCTCCC AGGGGAGGGT TTGCAAGGGT GAAAGGAGAG ACTGCCTGGC ACCCTGTGAG    11940
TGTCTGGGGA CAGTCTCGAT GACATTTACT GATAACCTGT GCGCCATGTC GCCCTCGCCC    12000
TCCTGGGGAA CTCTCAGGAC CCCCACCTCC TGCAGATGCC CCTCCCTGGT CCGACTCCCC    12060
TGGGACCTGA GCTGACCTGG ACGAGCAGAG CCCTGGGACA AGCTGGCTGC AGAGGCTGCC    12120
AGAGGGAGGC TGCCCCCATG GTTAGGCTAG GGGGTGGATT CTGCCTGGTG GGGGAAGGTC    12180
ACCCCACTCT TGACTGGCAG GAGAGACTGC TCTCCAGATC CCAGGTGAGA GAAGTGGCGT    12240
GGGTGGCAGG AGGAGCAGGG AGCCCACCCA GGGGCCAAGA GACCTGCAAA AAGTCCTGTC    12300
CCGTTTTCCA AAGCAGCACT GATGGAGCTC CTGGGAGAGC CTAGAGATTG CTGGGCCACA    12360
GGCACAGCAA AATGACACAT GGCTATACGG CATATGATGT GAAGTGGGGA TGGGTGGAGG    12420
GGGGGAGGTG GAGGGGGGAG AGGTGGAGAA GCAGTAGGGG TGTAATTAGA GGAGGGAGTG    12480
AATGGCCCAA GTCCCAGAGG GGACACTGAA GCCCCTTTTT TCTCTCCTGC TTTTTCCAGG    12540
ACATGCAAAG AGGCGCGTGC AGTGGGGGCC CTGGCCACCC TCCCCAGGCG CTGTTACTTA    12600
CTGCCAAAGG AACTGCAGCG GCACCTGTGG GAGAGAGAGG GGCTGAGCTG GCTGCCCCAG    12660
GGGAAAGGGG CCTGGGTGTC ACCTCCTGCA GAGGGGCCAG CAGGGCAGGG GAGCACCTGG    12720
AGGTGTCGCT CCCTCAAGAG CACCTGCTCC ACCACACAAC TGCTAGCAAT GATGATGACC    12780
TGCAGGGTGT GGGGACGGGG GTGGATTATC CCATCTCATC CTCACTTCAG CCCTGGGAGG    12840
GAGGAACCAC TATTGGCCCT ACTTGCAGAA GGAGACACTG AATCTCAGAG CCGTGACTTG    12900
CCCTTGGGGA CATGCTGGAC AGGTGCCAAA CGCTCCACTG GGAGCTTCAC ACGCACTCCT    12960
CCTCTTATTT CAGATTTTTG GGCCATCCAG TGCAGGAGAG GGACATCGTA TGGAGTGTTC    13020
```

-continued

```
CTGTCTAAGA  AGTGCAGTGT  GGCTGGAAAA  CTCACTGAGA  AGCCATGGGA  CGCGGCTGCC  13080
GCGGGTGGAG  TGCGTCCCAG  CTGCCAGGCA  CGGTGTGAGC  ATCCCCTACG  TAAATCGTGC  13140
CGTCCTCACA  AGAACCCTAT  GAGGGAACTT  CCTTATGGTC  CTGATTCTAC  AGCTGAGGAC  13200
ACACGGCTTG  GGGAGAAATA  TAGCCGAGAG  TGGGCGAGGC  CTGACCTGAA  TCCAGGTGTG  13260
TCTCTGTGTG  TCCAGGGGAT  GGGGGAGGCC  TATGATCCTG  GTGTGACCAG  GGGCCTTGAA  13320
ATCCCTGGGT  GAGATTCATC  AGAGTTGCAA  AAGGAAGGAG  CTGGTGCCAC  AGCTTTCCCC  13380
ACGGTGTTCC  CGAGAAAGGA  CGTGTGGGAT  TGGCAGTGGG  ATGTGTGGCC  CATGGGTTCT  13440
CCTGGGCAAG  CCAAGGCTGT  GGCCAGCAGG  ACAGGCAGGG  AGGCCTGGGC  AGGACAAGCC  13500
CATCCCCACC  CACTCCTTCC  TCTACCTCCA  TGTCTGGGCA  GCCACCTGCT  AGACCCTAGG  13560
ACACCTCGGG  GTGCAGCCAC  AGTAAGCAAG  GGCCAGGACT  GGGTGGTGAC  CAAGTGAGGC  13620
TCTGTGGGGA  CAGGCGGGAC  ATCAGGCAGG  GCACGGGGAG  GTCCTGGGGG  CTCCAAGTTG  13680
GGCCCTGGAG  GTGATGGGCT  GGCCAGGTGG  GGGCAGAGTG  GTGAGGAGGT  GGGAAGGCAT  13740
CGGGAGTGAG  GGCTGCTGCA  GGGCTGAGGA  TGGCATTGGG  AGAGACTTGG  AGCGGATGGA  13800
GGGAAGTTCA  AAGAACGTGG  CGGGAGGAGG  GTCTCCAGTC  AAGGTGACCC  CCAGACTTGC  13860
ACTTGGCATG  AATTC                                                      13875
```